(12) United States Patent
Szillat et al.

(10) Patent No.: US 11,844,848 B2
(45) Date of Patent: Dec. 19, 2023

(54) PHOTOCURABLE DENTAL COMPOSITION

(71) Applicant: DENTSPLY DETREY GMBH, York, PA (US)

(72) Inventors: Florian Szillat, Constance (DE); Maximilian Maier, Dusseldorf (DE); Caroline Renn, Singen (DE); Oliver Elsner, Radolfzell (DE); Joachim E. Klee, Radolfzell (DE); Jorg Kempter, Constance (DE); Jacques Lalevee, Mulhouse (FR); Mariem Bouzrati-Zerelli, Mulhouse (FR); Julie Kirschner, Dambach-la-Ville (FR)

(73) Assignee: DENTSPLY SIRONA INC., York, PA (US)

(*) Notice: Subject to any disclaimer, the term of this patent is extended or adjusted under 35 U.S.C. 154(b) by 0 days.

(21) Appl. No.: 16/754,263

(22) PCT Filed: Oct. 9, 2018

(86) PCT No.: PCT/EP2018/077383
§ 371 (c)(1),
(2) Date: Apr. 7, 2020

(87) PCT Pub. No.: WO2019/072787
PCT Pub. Date: Apr. 18, 2019

(65) Prior Publication Data
US 2021/0186821 A1    Jun. 24, 2021

(30) Foreign Application Priority Data
Oct. 13, 2017  (EP) .................................. 17196330

(51) Int. Cl.
A61K 6/62     (2020.01)
A61K 6/889    (2020.01)
(Continued)

(52) U.S. Cl.
CPC ................ *A61K 6/62* (2020.01); *A61K 6/889* (2020.01); *A61K 6/90* (2020.01); *C08L 33/08* (2013.01); *C08L 33/10* (2013.01)

(58) Field of Classification Search
CPC ...................................................... A61K 6/62
See application file for complete search history.

(56) References Cited

U.S. PATENT DOCUMENTS 3,534,122 A    10/1970  Cornell
3,729,313 A *  4/1973  Smith .................... G03F 7/029
                                                     430/332

(Continued)

FOREIGN PATENT DOCUMENTS

EP    0237233 A2    9/1987
EP    0329268 A2    8/1989
(Continued)

OTHER PUBLICATIONS

Three-Component Coupling Reactions of Silylglyoxylates, Alkynes, and Aldehydes: A Chemoselective One-Step Glycolate Aldol Construction; Nicewicz D.A. in Journal of American Chemical Society; 2005, 127 (17); pp. 6170-6171.

(Continued)

*Primary Examiner* — Michael F Pepitone
(74) *Attorney, Agent, or Firm* — DENTSPLY SIRONA INC.

(57) ABSTRACT

The present invention relates to a photocurable dental composition comprising a specific polymerization initiator system containing the combination of a photoinitiator compound and a coinitiator compound being a sulfinate compound or a sulfonate compound. The present invention also relates to the use of this polymerization initiator system in a photocurable dental composition.

23 Claims, 6 Drawing Sheets

(51) Int. Cl.
*A61K 6/90* (2020.01)
*C08L 33/08* (2006.01)
*C08L 33/10* (2006.01)

(56) References Cited

U.S. PATENT DOCUMENTS

| | | | | |
|---|---|---|---|---|
| 3,741,769 | A | * 6/1973 | Smith | G03F 7/029 |
| | | | | 522/182 |
| 4,503,169 | A | * 3/1985 | Randklev | A61K 6/887 |
| | | | | 106/35 |
| 5,545,676 | A | 8/1996 | Palazzotto | |
| 5,744,511 | A | * 4/1998 | Kazama | G03F 7/029 |
| | | | | 522/25 |
| 6,017,660 | A | * 1/2000 | Palazzotto | C08F 2/50 |
| | | | | 430/17 |
| 2003/0018098 | A1 | 1/2003 | Falsafi | |
| 2005/0070621 | A1 | 3/2005 | Kalgutkar | |
| 2005/0070624 | A1 | 3/2005 | Kalgutkar | |
| 2006/0247330 | A1 | 11/2006 | Takano | |
| 2009/0137697 | A1 | 5/2009 | Ori | |

FOREIGN PATENT DOCUMENTS

| | | | |
|---|---|---|---|
| EP | 0408357 | A2 | 1/1991 |
| EP | 1502569 | A1 | 2/2005 |
| EP | 1938781 | A1 | 7/2008 |
| EP | 2604247 | A1 | 6/2013 |
| WO | 1999062460 | A1 | 12/1999 |
| WO | 2017017155 | A1 | 2/2017 |
| WO | 2017060459 | A1 | 4/2017 |

OTHER PUBLICATIONS

Silyl Glyoxylates. Conception and Realization of Flexible Conjunctive Reagents for Multicomponent Coupling; Boyce G.R. et al. in Journal of Organic Chemistry; 2012, 77 (10); pp. 4503-4515.
Construction of Cyclopentanol Derivatives via Three-Component Coupling of Silyl Glyoxylates, Acetylides, and Nitroalkenes; Boyce G.R. et al. in Organic Letters; 2012, 14 (2); pp. 652-655.
Tert-Butyl Tert-Butyldimethylsilylglyoxylate: A Useful Conjunctive Reagent; Nicewicz D.A. et al. in Organic Synththeses, 2008, 85; pp. 278-286.
A search for new radical sources in photoinitiating sytems; El-Roz, M. et al. in Current Trends in Polymer Science 2011, vol. 15; pp. 1-13.
International Search Report; PCT/EP2018/077383; Dec. 6, 2018 (completed); dated Dec. 20, 2018.
International Preliminary Report on Patentability; PCT/EP2018/077383; Dec. 6, 2018 (completed); dated Dec. 20, 2018.
Written Opinion of the International Searching Authority; PCT/EP2018/077383; Dec. 6, 2018 (completed); dated Dec. 20, 2018.

* cited by examiner

PHOTOCURABLE DENTAL COMPOSITION

CROSS-REFERENCE TO RELATED APPLICATIONS

This application is a national stage of PCT/EP2018/077383, filed Oct. 9, 2018, which claims priority to European Patent Application No. 17196330.9, filed on Oct. 13, 2017, which is herein incorporated by reference for all purposes.

FIELD OF THE INVENTION

The present invention relates to a photocurable dental composition comprising a specific polymerization initiator system containing a combination of a photoinitiator compound and a specific sulfinate or sulfonate coinitiator. The present invention also relates to the use of the polymerization initiator system in a photocurable dental composition. The specific polymerization initiator system of the present invention has high stability in acidic media.

BACKGROUND OF THE INVENTION

Polymerizable compositions containing sulfinate compounds are known from EP-A 0 408 357, US-A 2005/070624, EP-A 0 237 233, and US-A 2009/137697.

The restoration of teeth commonly involves a photocurable dental composition containing free-radically and/or cationically polymerizable resins. Photocuring of a dental composition containing free-radically polymerizable resins involves a photoinitiator system generating free radicals upon exposure to visible light. Free radicals may be typically produced by either of two pathways:

(1) the photoinitiator compound undergoes excitation by energy absorption with subsequent decomposition of the compound into one or more radicals (Norrish type I), or (2) the photoinitiator compound undergoes excitation and the excited photoinitiator compound interacts with a second compound by either energy transfer or a redox reaction to form free radicals from any of the compounds (Norrish type II).

For a photoinitiator to be useful for use in a dental composition, the quantum yields indicating the conversion of light radiation to radical formation needs to be high, since absorption or shielding of light by further components of the dental composition limit the amount of energy available for absorption by the photoinitiators. Accordingly, only about 70 percent conversion of the polymerizable groups may be expected in a polymerization of a typical dental composition, whereby the mechanical strength of the polymerized dental composition is less than optimal and unreacted monomers may leach out of the polymerized dental composition. The leaching monomers may have detrimental effects. To alleviate this problem, multifunctional monomers are frequently used which are more likely to be included in the polymer network.

In addition, photoinitiators are required to have a high acid resistance, solubility, thermal stability, and storage stability when incorporated into a dental composition.

Finally, given that dental compositions usually contain (meth)acrylate or (meth)acrylamide monomers, free radical photocuring may be inhibited by the presence of oxygen. Oxygen inhibition is due to the rapid reaction of propagating radicals with oxygen molecules to yield peroxyl radicals which are not as reactive towards carbon-carbon unsaturated double bonds and therefore do not initiate or participate in any photopolymerization reaction. Oxygen inhibition may lead to premature chain termination and, therefore, incomplete photocuring. Nevertheless, a certain degree of oxygen inhibition on the top surface of the adhesive layer is required for the bonding to the adjacent restorative.

Accordingly, the photoinitiator system has a critical influence on the quality of the dental material. Conventionally, camphor quinone optionally in combination with a tertiary amine, or 2,4,6-trimethylbenzoylphenyl phosphinate (Irgacure® TPO) are frequently used as photoinitiator system. However, the presence of amines in acrylate-containing compositions can cause yellowing in the resulting photocured composition, create undesirable odors, and soften the cured composition because of chain transfer reactions and therefore, often require the use of stabilizers. Moreover, the use of aromatic amines gives rise to toxicological concerns.

Furthermore, it is desirable that the light activating of the photoinitiator system can be initiated at a sufficiently long wavelength in order to avoid damage of soft tissue during polymerization of the dental composition in the patient's mouth. Accordingly, the photoinitiator system is required to contain a chromophoric group efficiently absorbing light of the desired wavelength in a range of from 400 to 800 nm. However, an increase of the absorption coefficient of the photoinitiator system increases the coloration of the photoinitiator system and thereby the coloration of the dental composition before light curing. Accordingly, it is necessary that the chromophoric groups are efficiently destroyed during polymerization so that the coloration of the initiator system disappears in the polymerized dental composition, the so-called "photo-bleaching". A destruction of the chromophoric groups during polymerization may also be useful in increasing the depth of cure of the dental composition since activating light is not shielded from unpolymerized layers of the dental composition by the photoinitiator system present in polymerized layers covering the unpolymerized layers.

In conventional photocurable dental compositions, typically, organic phosphine compounds are contained as coinitiators, as disclosed for example in U.S. Pat. Nos. 3,534,122 A, 5,545,676 A, WO 1999062460 A1 and WO 2017/017155 A1.

Sulfinate compounds are typically used as reducing agents in redox curable dental compositions, as disclosed for example in EP 1 938 781 A1, EP 1 502 569 A1, US 20060247330 A1 and US 20030018098 A1.

However, hitherto, sulfinate compounds or sulfonate compounds were not used as coinitiators in photocurable dental compositions.

Sulfinate compounds are salts requiring cations providing solubility or dispersibility of the salt in a resin matrix. Given the hydrophobic nature of the resin matrix, suitable cations have a high molecular weight. Since the cations will not be incorporated into the polymer network, the cured dental composition, will contain a substantial amount of leachable coinitiator derived cations, which may give rise to toxicological concerns.

SUMMARY OF THE INVENTION

It is the problem of the present invention to provide a photocurable dental composition comprising one or more radical-polymerizable compounds, which composition provides improved stability in acidic media, high polymerization efficiency including a high conversion and good curing rate which may be adapted to provide a suitable working time of the composition, while coloration problems are absent. Moreover, leaching problems should preferably also be reduced or avoided.

Moreover, it is the problem of the present invention to provide a use of a specific polymerization initiator system in a photocurable dental composition.

The present invention provides a photocurable dental composition comprising
(a) one or more polymerizable compounds, and
(b) a polymerization initiator system containing
  (i) a photoinitiator compound having a light absorption maximum in the range from 300 to 800 nm; and
  (ii) a coinitiator compound;
wherein the coinitiator compound is a sulfinate compound or a sulfonate compound of the following formula (I):

$$(R—SO_x^-)_y M^{p+} \qquad (I)$$

wherein
R represents an organic moiety;
$M^{p+}$ is a cation,
x is 2 or 3,
y is an integer of from 1 to 4,
provided that when x is 2, then $M^{x+}$ is an iodonium ion of the following formula (II):

$$R^1—I^+—R^2 \qquad (II)$$

wherein
$R^1$ and $R^2$ which are independent from each other represent an organic moiety.

Furthermore, the present invention provides the use of a polymerization initiator system containing
(i) a photoinitiator compound having a light absorption maximum in the range from 300 to 800 nm; and
(ii) a coinitiator compound;
wherein the coinitiator compound is a sulfinate compound or a sulfonate compound of the following formula (I):

$$(R—SO_x^-)_y M^{p+} \qquad (I)$$

wherein
R represents an organic moiety;
$M^{p+}$ is a cation,
x is 2 or 3,
y is an integer of from 1 to 4, provided that when x is 2, then $M^{x+}$ is an iodonium ion of the following formula (II):

$$R^1—I^+—R^2 \qquad (II)$$

wherein
$R^1$ and $R^2$ which are independent from each other represent an organic moiety, in a photocurable dental composition.

The present invention is based on the recognition that the sulfinate compound or a sulfonate compound of formula (I) according to the present invention surprisingly acts as a highly efficient coinitiator for the photoinitiator compound (i). Thereby, the polymerization initiator system (ii) provides high stability in acidic media, improved polymerization efficiency, high curing speed and does not give rise to coloration problems of a photocurable dental composition. Accordingly, a large amount of the photocurable dental composition can be photocured with reduced exposure to radiation. Moreover, leaching of cationic species may preferably be reduced or avoided by the selection of suitable sulfinate salts.

BRIEF DESCRIPTION OF THE FIGURES

FIG. 3B shows photopolymerization profiles of methacrylate functions (Methacrylic Acid/BisGMA/TEGDMA: 10/63/27% w/w) in presence of (1)PI (1% w) (2)PI/Sulfinate (1/1% w/w) (3)PI/EDB (1/1% w/w) (4)PI/SulfinateIod (1/1/1% w/w) under exposure to Smartlite Focus (300 mW.cm$^{-2}$); sample thickness=1.4 mm; under air: PI=PPD. PI=photoinitiator.

CQ/iodonium sulfinate (0.5/1% w/w) in bisGMA/TEGDMA (70/30% w/w) (3) CQ/iodonium sulfinate (0.5/1% w/w) in Methacrylic acid/bisGMA/TEGDMA (10/63/27% w/w) (4) CQ/EDB (0.5/1% w/w) in bisGMA/TEGDMA (70/30% w/w) (5) CQ (0.5% w) in Methacrylic acid/bisGMA/TEGDMA (10/63/27% w/w). The irradiation starts at t=5 s.

Figure 8:
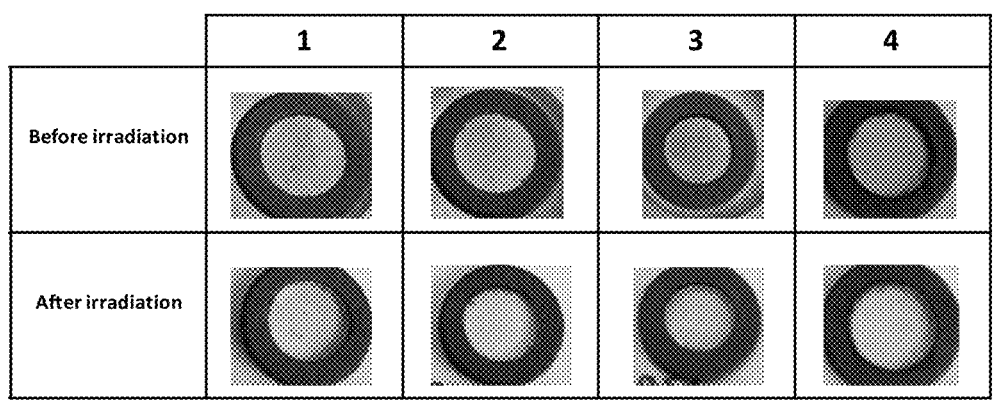

FIG. 8 shows photos of the samples before and after polymerization (under air; thickness=1.4 mm; Smartlite Focus (300 mW.cm$^{-2}$); 115 s irradiation): (1) CQ/iodonium sulfinate (0.5/1% w/w) in 2-hydroxyethyl methacrylate/bisGMA/TEGDMA (10/63/27% w/w) (2) CQ/iodonium sulfinate (0.5/1% w/w) in bisGMA/TEGDMA (70/30% w/w) (3) CQ/iodonium sulfinate (0.5/1% w/w) in Methacrylic acid/bisGMA/TEGDMA (10/63/27% w/w) (4) CQ/EDB (0.5/1% w/w) in bisGMA/TEGDMA (70/30% w/w).

Figure 9:
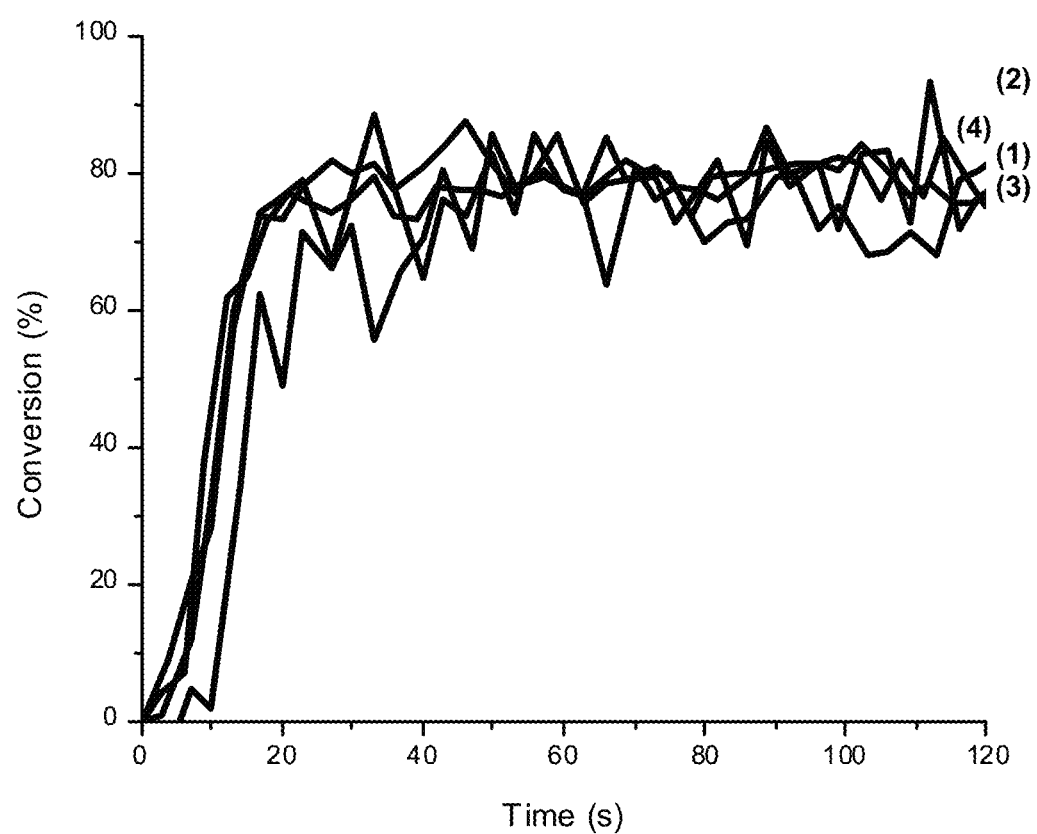

FIG. 9 shows photopolymerization profiles of methacrylate resins (bisGMA-TEGDMA or bisGMA-TEGDMA/2-hydroxyethyl methacrylate: 90/10% w/w or bisGMA-TEGDMA/Methacrylic acid: 90/10% w/w) in presence of camphorquinone as photoinitiator (under air; thickness=1.4 mm; Smartlite Focus 300 mW.cm$^{-2}$): (1) CQ/p-toluenesulfonate/Iod (0.5/1/1% w/w) in bisGMA/TEGDMA (70/30% w/w); (2) CQ/p-toluenesulfonate/Iod (0.5/1/1% w/w) in 2-hydroxyethyl methacrylate/bisGMA/TEGDMA (10/63/27% w/w); (3) CQ/p-toluenesulfonate/Iod (0.5/1/1% w/w) in Methacrylic acid/bisGMA/TEGDMA (10/63/27% w/w); (4) CQ/EDB (0.5/1% w/w) in bisGMA/TEGDMA (70/30% w/w). The irradiation starts at t=5 s.

Figures 10, 11:
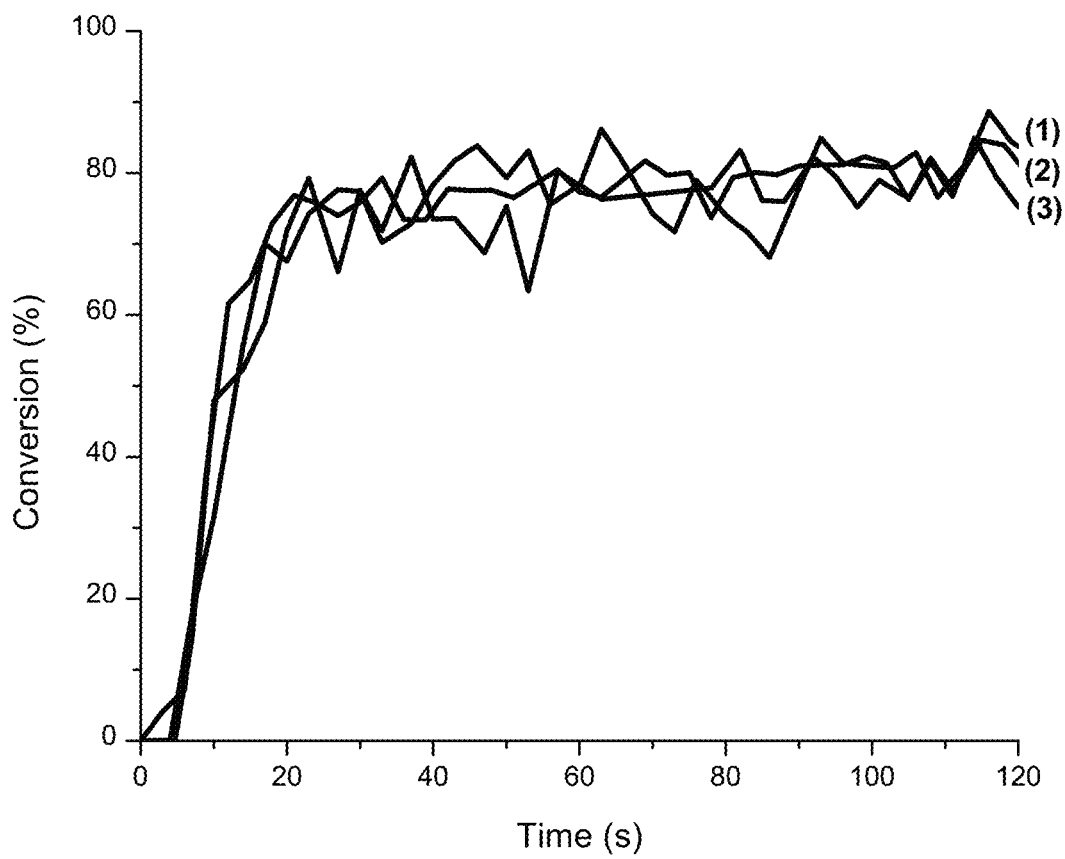

FIG. 10 shows photopolymerization profiles of methacrylate resins (bisGMA-TEGDMA or bisGMA-TEGDMA/2-hydroxyethyl methacrylate: 90/10% w/w) in presence of camphorquinone as photoinitiator (under air; thickness=1.4 mm; Smartlite Focus (300 mW.cm$^{-2}$): (1) CQ/iodonium sulfonate (0.5/1% w/w) in bisGMA/TEGDMA (70/30% w/w); (2) CQ/iodonium sulfonate (0.5/1% w/w) in 2-hydroxyethyl methacrylate/bisGMA/TEGDMA (10/63/27% w/w) (3) CQ/EDB (0.5/1% w/w) in bisGMA/TEGDMA (70/30% w/w). The irradiation starts at t=5 s.

FIG. 11 shows photos of the samples before and after polymerization (under air; thickness=1.4 mm; Smartlite Focus (300 mW.cm$^{-2}$); 115 s irradiation). CQ(0.5% w/w); Iod (1% w/w); sulfonate (1% w/w).

DETAILED DESCRIPTION OF PREFERRED EMBODIMENTS

The terms "polymerization" or "polymerizable" relate to the combining by covalent bonding of many smaller molecules, such as monomers in the form of radical-polymerizable or cationically polymerizable compounds, to form larger molecules, that is, macromolecules or polymers. The monomers may be combined to form only linear macromolecules or they may be combined to form three-dimensional macromolecule, commonly referred to as crosslinked polymers. In case of a higher conversion rate of the polymerizable monomer, the amount of multifunctional monomers may be reduced or the leaching problem may be alleviated.

The term "photocurable" refers to a dental composition that will radically and/or cationically polymerize into a crosslinked polymer network when irradiated for example with actinic radiation such as ultraviolet (UV), visible, or infrared radiation. "Actinic radiation" is any electromagnetic radiation that is capable of producing photochemical action and can have a wavelength of at least 150 nm and up to and including 1250 nm, and typically at least 300 nm and up to and including 750 nm.

The term "radical-polymerizable" as used herein in connection with compounds (a) means any compound capable of radical polymerization. Typically, compounds (a) are radical-polymerizable due to a polymerizable double bond, preferably one or more carbon-carbon double bonds. Examples of the polymerizable double bond include vinyl, conjugated vinyl, allyl, acryl, methacryl and styryl. More preferably, the polymerizable double bound is selected from the group consisting of acryl, methacryl and styryl. Acryl and methacryl may be (meth)acryloyl or (meth)acrylamide. Most preferably, for compounds (a), the polymerizable double bound is acryl or methacryl.

The term "cationically polymerizable" as used herein in connection with compounds (a) means any compound capable of cationic polymerization. Typically, compounds (a) are cationically polymerizable due to the presence of a functional group having a carbon-carbon double bond such as a vinyl ether group.

The term "polymerization initiator system" refers to a system comprising (i) a photoinitiator compound and (ii) a coinitiator compound. Optionally, the polymerization initiator system may further comprise (iii) an electron-donor.

The term "photoinitiator" used in connection with the compound (i) refers to a compound that is activated, for example by forming free radicals, typically by exposure to light or interaction with another compound such as coinitiator compound (ii) and/or electron-donor (iii) in a photochemical process.

The term "electron donor" as used herein means a compound which is capable of donating electrons in a photochemical process. Suitable examples include organic compounds having heteroatoms with electron lone pairs, for example amine compounds or organic hydrides of Ge, Si and Sn. Preferred electron donors are organic hydrides of Ge, Si and Sn.

The present invention relates to a photocurable dental composition. The photocurable dental composition may be a dental composite, a dental glass ionomer cement, a dental cement or a dental impression material.

The Polymerizable Compounds (a)

The photocurable dental composition comprises (a) one or more polymerizable compounds. The compounds may be radical-polymerizable or cationically polymerizable.

The one or more radical-polymerizable compounds (a) may preferably be radical-polymerizable N-substituted alkyl acrylic or acrylic acid amide monomers or a (meth)acrylate compounds.

A radical-polymerizable N-substituted alkyl acrylic or acrylic acid amide monomer may be preferably selected from compounds characterized by one of the following formulae (X), (XI) and (XII):

(X)

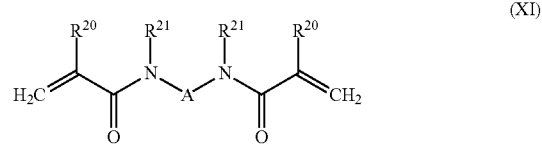

(XI)

$$\left[H_2C \underset{O}{\overset{R^{20}}{\diagdown}} \underset{}{\overset{R^{21}}{\diagdown}} N \right]_n Z. \qquad (XII)$$

In formulae (X), (XI) and (XII), $R^{20}$, $R^{21}$ and $R^{22}$ independently represent a hydrogen atom or a C1 to C8 alkyl group; A represents a divalent substituted or unsubstituted organic residue having from 1 to 10 carbon atoms, whereby said organic residue may contain from 1 to 3 oxygen and/or nitrogen atoms; Z represents a saturated at least trivalent substituted or unsubstituted C1 to C8 hydrocarbon group, a saturated at least trivalent substituted or unsubstituted cyclic C3 to C8 hydrocarbon group, and n is at least 3.

Preferably, the one or more radical-polymerizable compounds (a) include bisacrylamides such as N,N'-diethyl-1,3-bisacrylamido-propan (BADEP), 1,3-bisacrylamido-propan (BAP), 1,3-bisacrylamido-2-ethyl-propan (BAPEN), N,N'-(2E)-2-butene-1,4-diylbis[N-2-propen-1-yl-2-propenamide] (BAABE), N,N-di(cyclopropyl acrylamido) propane (BCPBAP) and N,N'-(2-hydroxy-1,3-propanediyl)bis[N-2-propen-1-yl-2-propenamide] (DAAHP).

Alternatively or additionally, for the one or more radical-polymerizable compounds (a), a (meth)acrylate compound may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono-and di- acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of radical-polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

Preferably, the one or more radical-polymerizable compounds (a) contain one or two radical-polymerizable groups, more preferably two radical-polymerizable groups, such as bisacrylamides like BADEP, BAP, BAPEN, BAABE, BCPBAP and DAAHP.

It is preferable that a blending ratio of the one or more radical-polymerizable compounds (a) to the entire photocurable dental composition is 5 to 80% by weight. More preferably, the blending ratio is 10 to 60% by weight.

A suitable cationically polymerizable compound may be selected from vinyl ether compounds.

The Polymerization Initiator System (b)

The photocurable dental composition further comprises a polymerization initiator system (b).

The polymerization initiator system (b) comprises (i) an photoinitiator compound having a light absorption maximum in the range from 300 to 800 nm, in particular 350 to 500nm. The polymerization initiator system (b) may comprise one or a mixture of two or more photoinitiator compound(s) (i).

Suitable 1,2-diketone photoinitiator compounds (i) may be selected from the group consisting of camphorquinone, benzil, 2,2'-3 3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Camphorquinone is preferred.

Alternatively or additionally, the photoinitiator compound (i) may be selected from Si- or Ge-acyl compounds having the following formula (V):

$$X-R^9 \qquad (V)$$

wherein
X is a group of the following formula (VI):

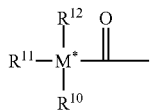

(VI)

wherein
M* is Si or Ge;
R¹⁰ represents a substituted or unsubstituted hydrocarbyl or hydrocarbylcarbonyl group;
R¹¹ represents a substituted or unsubstituted hydrocarbyl or hydrocarbylcarbonyl group;
R¹² represents a substituted or unsubstituted hydrocarbyl group; and
R⁹ i) has the same meaning as X, whereby the compound of formula (V) may be symmetrical or unsymmetrical; or
ii) is a group of the following formula (VII):

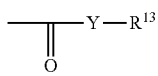

(VII)

wherein
Y represents a single bond, an oxygen atom or a group NR', wherein R' represents a substituted or unsubstituted hydrocarbyl group;
R¹³ represents a substituted or unsubstituted hydrocarbyl group, a trihydrocarbylsilyl group, a mono(hydrocarbyl-carbonyl)dihydrocarbylsilyl group or a di(hydrocarbyl-carbonyl)mono-hydrocarbylsilyl group.

It was surprisingly found that Si- or Ge-acyl compounds of formula (V) represent 1,2-diketone photoinitiators which are particularly suitable for dental compositions. With compounds of formula (V), a high polymerization efficiency is attained, and no coloration problems occur, or in a polymerization system comprising a conventional photoinitiator such as camphor quinone, coloration is efficiently suppressed. Furthermore, compounds of formula (V) have a light absorption within the wavelength range typically applied in dental application, they are compatible with the ingredients of dental compositions and besides, they are considered physiologically harmless.

Therefore, in the polymerization initiator system (b), Si- or Ge-acyl compounds of formula (V) are particularly preferred as 1,2-diketone photoinitiator compound (i).

In connection with the Si- or Ge-acyl compound of formula (V), the term "substituted" as used herein means that R¹⁰, R¹¹, R¹², R¹³ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —NR$^x$R$^y$ group wherein R$^x$ and R$^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —NR$^x$R$^y$ group wherein R$^x$ and R$^y$ independently from each other represent a $C_{1-4}$ alkyl group.

If R¹⁰, R¹¹ and R¹² are substituted, then it is preferred that they are substituted with 1 to 3 substituents, more preferably with 1 substituent.

In the compound of formula (V), moieties R¹⁰, R¹¹ and R¹² may be defined as follows:

R¹⁰ and R¹¹ independently from each other represent a substituted or unsubstituted hydrocarbyl or hydrocarbylcarbonyl group, and R¹² represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl(-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of R¹⁰ and R¹¹ represent acyl groups ($R_{org}$—(C=O)—) in which the organic residue $R_{org}$ is a hydrocarbyl residue as defined above.

Compound of formula (V) may contain one or two hydrocarbylcarbonyl groups, that is either one of R¹⁰ or R¹¹ is a hydrocarbylcarbonyl group, or both R¹⁰ and R¹¹ are hydrocarbylcarbonyl groups. Preferably, compound of formula (V) contains one hydrocarbylcarbonyl group.

Preferably, the hydrocarbylcarbonyl group is an arylcarbonyl group, more preferably a benzoyl group.

Preferably, R¹⁰ and R¹¹ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —NR$^x$R$^y$ group wherein R$^x$ and R$^y$ independently from each other represent a $C_{1-4}$ alkyl group, and R¹² is a straight chain or branched $C_{1-6}$ alkyl group or a phenyl group.

Most preferably, R¹⁰ and R¹¹ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^{12}$ is a straight chain or branched $C_{1-4}$ alkyl group.

In the compound of formula (V), $R^9$ may have the same meaning as X, whereby the compound of formula (V) may be symmetrical or unsymmetrical. Alternatively, $R^9$ may represent a substituted or unsubstituted hydrocarbyl group, or a group of formula (VII). Preferably, if $R^9$ has the same meaning as X, then compound of formula (V) is unsymmetrical. If $R^9$ represents a substituted or unsubstituted hydrocarbyl group, then the hydrocarbyl group has the same meaning as defined above for $R^{10}$ and is independently selected therefrom.

In the group of formula (VII) of compound of formula (V), $R^{13}$ represents a substituted or unsubstituted hydrocarbyl group, a trihydrocarbylsilyl group, a mono(hydrocarbylcarbonyl)-dihydrocarbylsilyl group or a di(hydrocarbylcarbonyl)monohydrocarbylsilyl group.

If $R^{13}$ of formula (VII) is a trihydrocarbylsilylgroup, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^{10}$, $R^{11}$ and $R^{12}$ and is independently selected therefrom.

In formula (VII), R' has the same meaning as defined for $R^{12}$ and is independently selected therefrom.

For example, compounds of formula (V) wherein $R^9$ has the same meaning as X and which are symmetrical may be have the following structural formulae:

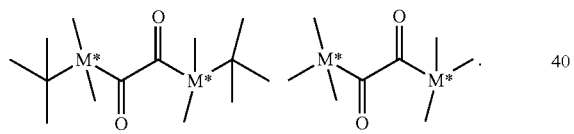

For example, compounds of formula (V) wherein $R^9$ represents a group of formula (VII) wherein Y is a bond, an oxygen atom or a NR' group, and $R^{13}$ represents a substituted or unsubstituted hydrocarbyl group may have the following structural formulae:

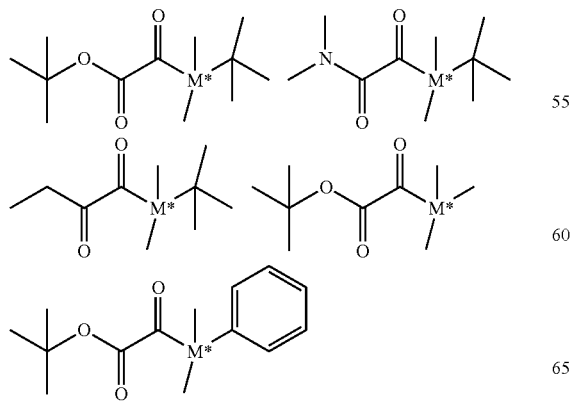

-continued

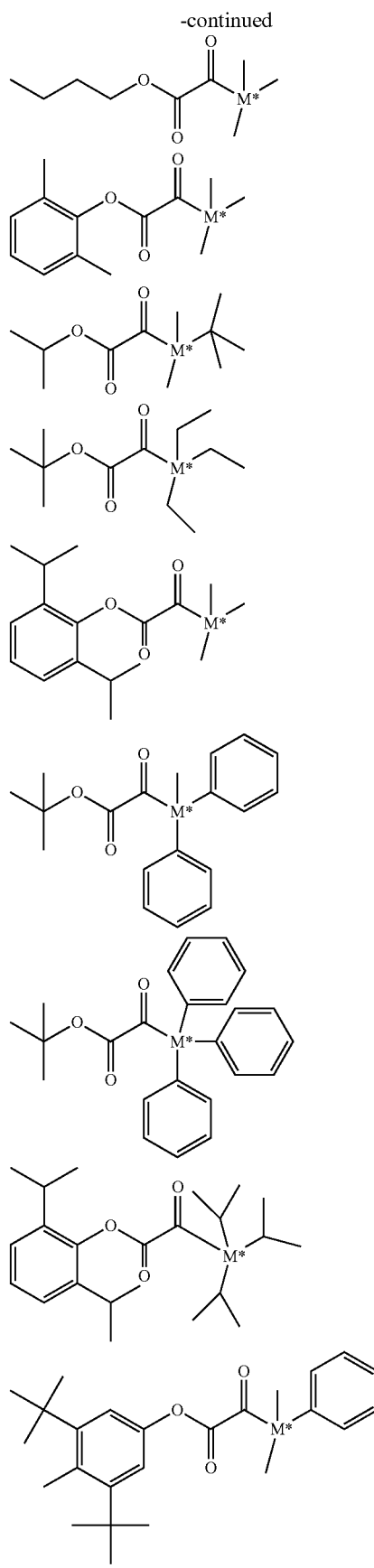

For example, compounds of formula (V) wherein $R^9$ represents a group of formula (VII) wherein $R^{13}$ represents a trihydrocarbylsilyl group have the following structural formulae:

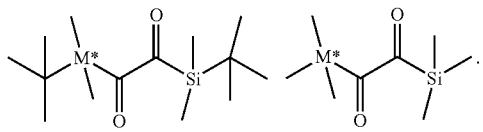

Preferably, compound of formula (V) is selected from the group consisting of:

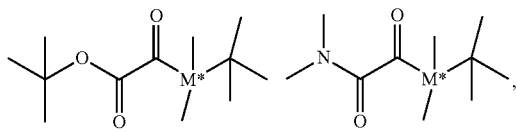

wherein compounds of formula (V) with M*=Si are particularly preferred.

More preferably, compound of formula (V) has the following structural formula:

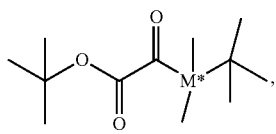

wherein it is particularly preferred that M*=Si. That is, tert-butyl (tert-butyldimethylsilyl)-glyoxylate) (DKSi) is particularly preferred.

In case the photocurable dental composition is in the form of an acidic composition, that is a composition having a pH of less than 7, depending on the composition's pH level, it is preferred to select compounds of formula (V) with the proviso that they do not contain ester groups, or at least only ester groups which do not significantly hydrolyse in aqueous media at pH 3 at room temperature within one month. Thereby, an advantageous stability of an acidic photocurable dental composition, that is a composition having a pH of less than 7, in terms of shelf-life stability of the uncured photocurable dental composition as well as stability after curing in the mouth of a patient is ensured. Therefore, for acidic photocurable dental compositions, particularly preferred are compounds of formula (V) excluding $R^9$ being a group of formula (VII) in which Y is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (V) may be a known compound which is commercially available or a may be prepared according to published procedures.

The compound of formula (V) wherein $R^9$ represents a group of formula (VII) in which Y is an oxygen atom and $R^{13}$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyl-trifluoromethane-sulfonate to obtain a trihydrocarbylsilyldiazoacetate, which is finally reacted with potassium peroxymonosulfate to arrive at the target compound:

Scheme 1 Preparation of silylglyoxylates

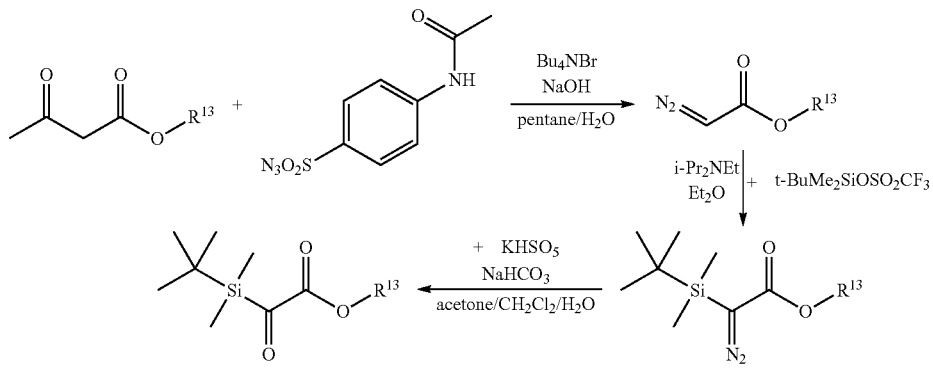

In Scheme 1, the reaction is exemplary depicted for obtaining a compound of formula (V) wherein in X of formula (V), $R^{10}$ and $R^{11}$ represent a methyl group, and $R^{12}$ represents a tert-butyl group. It is understood that $R^{10}$, $R^{11}$ and $R^{12}$ can be varied by applying a trihydrocarbylsilyltrifluoromethane-sulfonate other than t-BuMe$_2$SiOSO$_2$CF$_3$. Alternatively, compounds of formula (V) wherein M* is Si, $R^9$ represents a group of formula (VII) and Y represents an oxygen atom may be prepared by a single-pot three-component coupling reaction of a silylglyoxylate, a terminal alkyne and an aldehyde in the presence of ZnI$_2$ and Et$_3$N as described by Nicewicz D. A. in J. Am. Chem. Soc., 2005, 127 (17), pages 6170 to 6171. Further syntheses of silylglyoxylate compounds are described e.g. by Boyce G. R. et al. in *J. Org. Chem.*, 2012, 77 (10), pages 4503 to 4515 and Boyce G. R. et al. in Org. Lett., 2012, 14 (2), pages 652 to 655.

For example, the following compounds of formula (V) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-

71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

All compounds of formula (V) comprise the group of formula (VI)

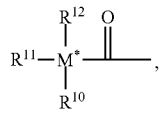
(VI)

wherein M*, $R^{10}$, $R^{11}$ and $R^{12}$ are defined as above. Depending on the selection of M*, the group of formula (VI) represents an acylsilane or acylgermane group. Upon eYosure to UV-VIS-light, the bond between M* and the acyl group may be cleaved, whereby a silyl/germanyl and an acyl

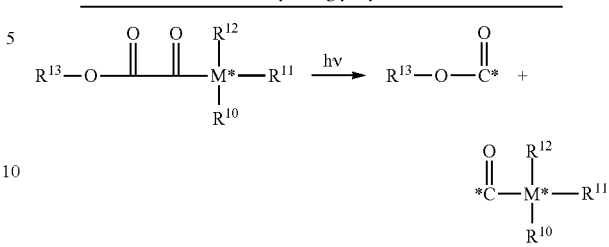

radical is formed as a polymerization initiating structure, but in competition to the cleavage into to radicals, a carbene structure might be formed:

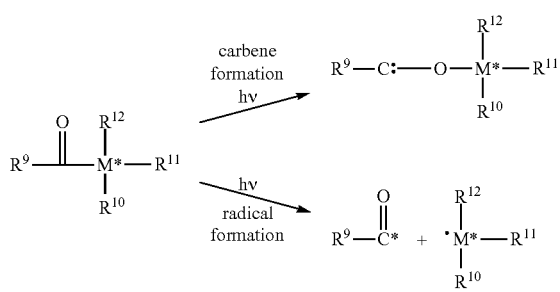

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (V) wherein $R^9$ has the same meaning as X or is a group of formula (VII), the C—C bond of the 1,2-diketone moiety (—C(=O)—C(=O)—) may be cleaved upon exposure to UV-VIS-light into two acyl radicals. This cleavage is exemplary shown for compound of formula (V) wherein $R^9$ is a group of formula (VII) and Y is an oxygen atom, that is for a glyoxylate (—O—C=O)—C(=O)—) compound:

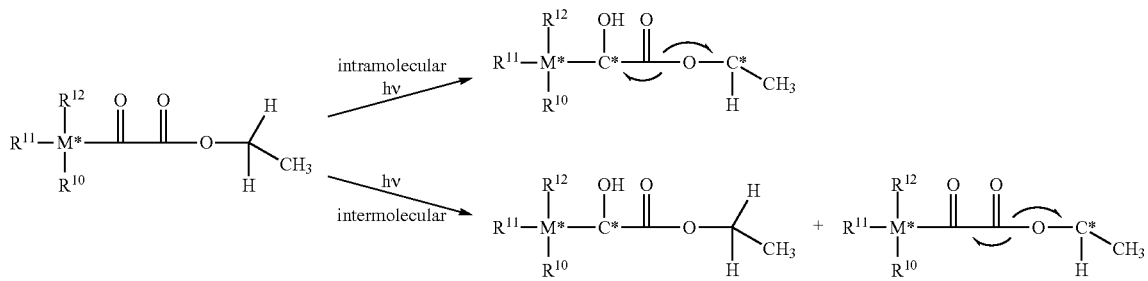

Besides, in compound of formula (V), there is a third possibility for a radical cleavage in case $R^9$ is a compound of formula (VII) wherein Y is an oxygen atom and $R^{13}$ is a substituted or unsubstituted hydrocarbyl group. Namely, an intra- or intermolecular hydrogen abstraction might occur, where a hydrogen radical is abstracted:

Both the cleavage of a glyoxylate group and the hydrogen abstraction mechanism is known for photoinitiators which do not contain silicium or germanium, such as ethyl phenylglyoxylate (Irgacure® MBF).

For compounds of formula (V) wherein $R^9$ has the same meaning as X or is a group of formula (VII), the present inventors carried out molecular modeling calculations which results are disclosed in WO 2017/060459 A1. From these molecular modeling calculations, it appears that a Si—C or Ge—C bond cleavage can be ruled out, since the C—C bond of the —C(=O)—C(=O)— moiety is weaker than the Si—C or Ge—C bond.

It is particularly preferred that the photoinitiator compound (i) is camphorquinone or DKSi.

Preferably, the photocurable dental composition comprises 0.05 to 5 mole percent of the photoinitiator compound (i) based on the one or more radical-polymerizable compounds (a).

In addition to the photoinitiator compound (i), the polymerization initiator system may comprise further photoinitiator compounds. Examples of suitable further photoinitiator compounds are 1,2-diketones, 1,3-diketones or phosphine oxides.

Preferred 1,3-diketones are for example dibenzoyl methane, benzoyl acetone and acetyl propionyl methane.

Examples of suitable phosphine oxides include 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X).

In addition to the photoinitiator compound (i) and optional further photoinitiator compounds, the polymerization initiator system (b) further contains a coinitiator compound (ii) being a sulfinate compound or a sulfonate compound of the following formula (I):

$(R—SO_x^-)_y M^{p+}$ (I)

wherein
R represents an organic moiety;
$M^{p+}$ is a cation,
x is 2 or 3,
y is an integer of from 1 to 4.

In the sulfinate compound of formula (I), x is 2. When x is 2, then $M^{x+}$ is an iodonium ion of the following formula (II):

$R^1—I^+—R^2$ (II)

wherein
$R^1$ and $R^2$ which are independent from each other represent an organic moiety.

In the sulfonate compound of formula (I), x is 3.

The polymerization initiator system (b) may contain one or a mixture of two or more coinitiator compounds (ii).

Preferably, in the sulfinate compound of formula (I), R is an aromatic or aliphatic organic moiety.

According to a preferred embodiment, in the sulfinate compound of formula (I), R is preferably an aromatic moiety, more preferably a phenyl or naphthyl group which may be substituted by 1 to 5 substituents, which may be the same or different and which are independently selected from a $C_{1-6}$ alkyl group, a hydroxyl group, an amino group, a halogen atom, and a carboxyl group.

According to an alternative preferred embodiment, in the sulfinate compound of formula (I), R is preferably an aliphatic moiety, more preferably a $C_{1-6}$ alkyl group which may be substituted by a phenyl or naphthyl group which may be substituted by 1 to 5 substituents, which may be the same or different and which are independently selected from a $C_{1-6}$ alkyl group, a hydroxyl group, an amino group, a halogen atom, and a carboxyl group.

Surprisingly, the combination of the photoinitiator compound (i) and the coinitiator compound (ii) has a synergistic effect in that it provides for an improved polymerization efficiency including a high conversion and good curing rate which may be adapted to provide a suitable working time of the composition, while both coloration problems are absent.

In the sulfinate compound or sulfonate compound of formula (I), $M^{p+}$ may be any cation suitable for dental compositions, for example a metal cation such as an alkali or alkaline earth metal, or an organic cation such as a iodonium ion, a sulfonium ion or a phosphonium ion.

Preferably, $M^{p+}$ is selected from
(1) an iodonium ion of the following formula (II):

$R^1—I^+—R^2$ (II)

wherein
$R^1$ and $R^2$ which are independent from each other represent an organic moiety;
(2) a sulfonium ion of the following formula (III):

$R^3R^4R^5S^+$ (III)

wherein
$R^3$, $R^4$ and $R^5$ which are independent from each other, represent an organic moiety, and optionally any two of $R^3$, $R^4$ and $R^5$ form a cyclic structure together with the sulfur atom to which they are bound;

(3) a phosphonium ion of the following formula (IV):

$R^6R^7R^8P^+$ (IV)

wherein
$R^6$, $R^7$ and $R^8$ which are independent from each other, represent an organic moiety.

By selecting $M^{p+}$ from formulae (II), (III) and (IV), the efficiency of the sulfinate compound or sulfonate compound of formula (I) as a coinitiator is significantly improved, whereby the polymerization performance of the polymerization initiator system (b) is also significantly improved.

Furthermore, in addition, it was surprisingly found that owing to the preferred selection of cation $M^{p+}$ from formula (II), (III) and (IV), the stability of the sulfinate compound or the sulfonate compound of formula (I), can be improved. Thereby, in turn, the storage stability of the photocurable dental composition can be improved.

Preferably, $R^1$ and $R^2$ of the iodonium ion of formula (II), $R^3$, $R^4$ and $R^5$ of the sulfonium ion of (III), and $R^6$, $R^7$ and $R^8$ of the phosphonium ion of formula (IV) are respectively selected from an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

More preferably, $R^1$ and $R^2$ of the iodonium ion of formula (II) and $R^3$, $R^4$ and $R^5$ of the sulfonium ion of (III) are respectively selected from a phenyl group which may be substituted with 1 to 3 substituents selected from halogen atoms, a cyano group, a hydroxy group, an amino group, $C_{1-6}$ alkyl groups and $C_{1-6}$ alkoxy groups. Preferably, R' is a linear, branched or cyclic alkyl group having 1 to 6 carbon atoms, which may be substituted with 1 to 3 groups selected from halogen atoms, a cyano group, a hydroxy group, an amino group, $C_{1-6}$ alkyl groups and $C_{1-6}$ alkoxy groups.

According to a preferred embodiment, the iodonium ion of formula (II) is a diaryl iodonium ion. Examples of useful diaryl iodonium ions include (4-methylphenyl)[4-(2-methylpropyl) phenyl] iodonium, diphenyliodonium tetrafluoroborate, di(4-methylphenyl)iodonium, phenyl-4-methylphenyliodonium, di(4-heptylphenyl)iodonium, di(3-nitrophenyl)iodonium, di(4-chlorophenyl)iodonium, di(naphthyl)iodonium, di(4-trifluoromethylphenyl)iodonium, diphenyliodonium, di(4-methylphenyl)iodonium; diphenyliodonium, di(4-phenoxyphenyl)iodonium, phenyl-2-thienyliodonium, 3,5-dimethylpyrazolyl-4-phenyliodonium, diphenyliodonium, 2,2'-diphenyliodonium, di(2,4-dichlorophenyl)iodonium, di(4-bromophenyl)iodonium, di(4-methoxyphenyl)iodonium, di(3-carboxyphenyl)iodonium, di(3-methoxycarbonylphenyl)iodonium , di(3-methoxysulfonylphenyl)iodonium, di(4-acetamidophenyl)iodonium , di(2-benzothienyl)iodonium, and diphenyliodonium.

More preferably aromatic iodonium ions of formula (II) are selected from the group consisting of diaryliodonium, (4-methylphenyl)[4-(2-methylpropyl) phenyl] iodonium, 4-octyloxyphenyl phenyliodonium, and 4-(1-methylethyl)

phenyl 4-methylphenyliodonium. Most preferably, the aromatic iodonium ion of formula (II) is diphenyliodonium or (4-methylphenyl)[4-(2-methylpropyl)phenyl]iodonium.

A preferred sulfonium ion of formula (III) is S-(phenyl) thianthrenium of the following formula:

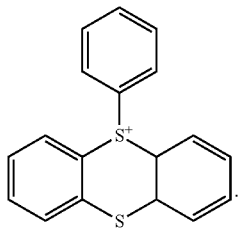 [SMILES: C1=CC2Sc3ccccc3[S+](c3ccccc3)C2C=C1]

Preferably, in a phosphonium ion of formula (IV), $R^6$, $R^7$ and $R^8$ independently from each other represent an aliphatic group, more preferably a straight chain or branched alkyl group having 1 to 6 carbon atoms which may be substituted by one or more aromatic groups, alicyclic groups having 3 to 6 carbon atoms, halogen atoms, hydroxyl groups or amino groups.

More preferably, in a phosphonium ion of formula (IV), $R^6$, $R^7$ and $R^8$ independently from each other represent a straight chain or branched alkyl group having 1 to 4 carbon atoms which may be substituted by one or more halogen atoms, hydroxyl groups or amino groups.

A particularly preferred phosphonium ion of formula (IV) is tetrakis-(hydroxymethyl)-phosphonium (THP).

A sulfinate compound or a sulfonium compound of formula (I) having $M^{y+}$ selected from a iodonium, sulfonium and phosphonium ion of formulae (II) (III) or (IV) may for example be prepared by reacting a hydroxide ($OH^-$) salt of iodonium, sulfonium and phosphonium ion of formulae (II) (III) or (IV) with a sulfinic acid $R$—$SO_2H$ or sulfonic acid in which R is defined as above for compound of formula (I).

Preferably, the photocurable dental composition comprises 0.05 to 5 mole percent of the coinitiator compound (ii) based on the one or more radical-polymerizable compounds (a).

Preferably, the polymerization initiator system (b) of the photocurable dental composition further comprises (iii) an electron-donor. Preferred electron-donors (iii) include, for example, amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid, or an organic hydride compound of Si, Ge or Sn.

More preferably, the electron-donor (iii) is an amine compound or an organic hydride compound of Si, Ge or Sn.

Preferred amine compounds are tertiary amine compounds, more preferably tertiary amine compounds selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. Most preferably, the tertiary amine compound is selected from the group consisting of triethanolamine, methyl 4-N,N-dimethylaminobenzoate, ethyl 4-N,N-dimethylaminobenzoate, 4-N,N-dimethylaminoethyl methacrylate and isoamyl 4-N,N-dimethylaminobenzoate.

Preferred organic hydride compounds of Si, Ge or Sn have the following formula (VIII):

$$L\text{-}H \qquad (VIII),$$

wherein L is a moiety of the following formula (IX):

$$R^a R^b R^c X^*\text{—} \qquad (IX).$$

In formula (IX), $X^*$ represents Si, Ge, or Sn, $R^a$ represents a hydrogen atom, an organic moiety or a different moiety L, and $R^b$ and $R^c$, which are independent from each other, represent an organic moiety.

The organic hydride compound of Si, Ge or Sn of formula (VIII) is a metal hydride and thus may react as a hydrogen donating agent in a photoexcitation complex with the photoinitiator compound (i). Accordingly, when the photoinitiator compound (i) absorbs visible light and forms an exciplex with the organic hydride compound of Si, Ge or Sn of formula (VIII), a hydrogen transfer may take place from the metal hydride to the photoinitiator (i), whereby the organic hydride compound of Si, Ge or Sn of formula (VIII) is transformed into a radical specifies capable of facilitating the polymerization reaction.

In formula (IX), $X^*$ represents Si, Ge, or Sn. Preferably, $X^*$ represents Si or Ge. More preferably, $X^*$ is Ge. According to a specific embodiment, the compound of formula (VIII) is a silane compound. According to a further specific embodiment, the compound of formula (VIII) is a germane compound.

In formula (IX), $R^a$ may be a hydrogen atom, an organic moiety or a different moiety L. When $R^a$ is a hydrogen atom, then the compound of formula (VIII) contains two metal hydride bonds ($X^*$—H). In case $R^a$ is a hydrogen atom, the $X^*$ is Si.

When $R^a$ represents an organic moiety, $R^a$ is preferably an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

When $R^a$ is a different moiety L, the compound of formula (VIII) of the formula (VIII) contains a metal-metal bond. In case two moieties L are present, then each $X^*$, $R^a$, $R^b$ and $R^c$ may be the same or different and independently has the meaning as defined by the present invention.

$R^b$ and $R^c$, which are independent from each other, represent an organic moiety. An organic group may be an aromatic, an aliphatic or an alicyclic group. An aromatic group may be a phenyl group. The phenyl group may be substituted by one or more straight chain or branched alkyl groups having 1 to 6 carbon atoms, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, $R^a$, $R^b$, and $R^c$ of formula (IX) are the same and represent an aliphatic, an aromatic or an alicyclic hydrocarbon group.

According to a preferred embodiment, the compound of formula (VIII) is selected from the following formulae:

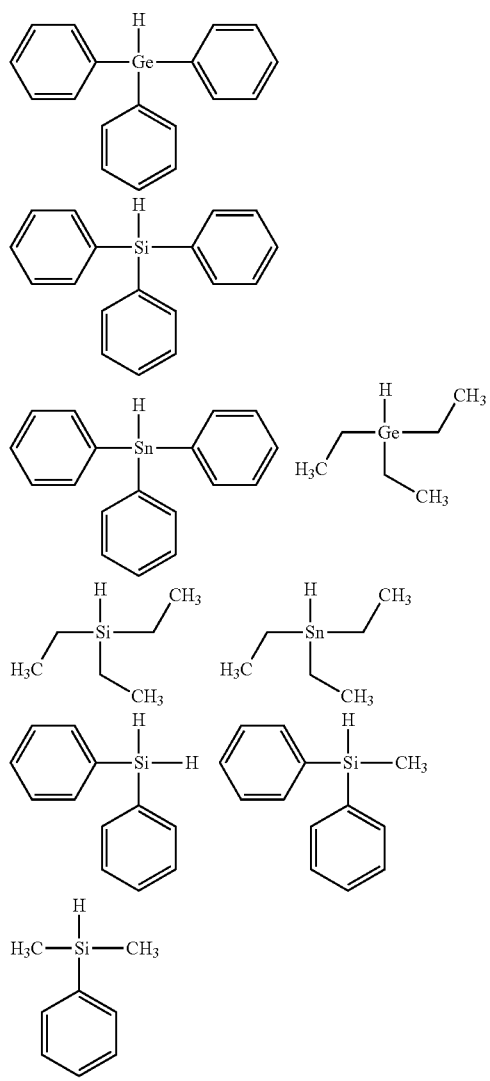

According to a preferred embodiment, the photocurable dental composition contains the compound of formula (VIII) in an amount from 0.05 to 5 percent by weight based on the total weight of the composition.

Preferably, in the polymerization initiator system (b) comprising component (i), (ii), and optionally (iii), the molar ratio ((i):(ii):(iii)) is 1:(0.1 to 10.0):(0.0 to 5.0), more preferably 1:(0.1 to 6.5):(0.0 to 4.0), even more preferably 1:(0.1 to 3.0):(0.0 to 3.0). On the one hand, when the amount of the coinitiator compound (ii) is below the above indicated lower limit of 0.1, then the conversion rate of the radical-polymerizable compounds (a) may decrease, and the reaction rate of the polymerization reaction may be low. By means of the addition of the optional electron-donor (iiii), both conversion rate and polymerization rate may be further advantageously adjusted.

Preferably, the photocurable dental composition according to the invention does not comprise a redox initiator. A redox initiator is a combination of an oxidizing agent and a reducing agent, which combination provides for a redox reaction in which radicals are formed. That is, such preferred photocurable dental composition according to the invention is exclusively cured by photocuring. Because, owing to the advantageous present polymerization initiator system (i) providing for improved polymerization efficiency, it can be dispensed with a redox initiator, i.e. a dual cure composition.

Further Components

Optionally, the photocurable dental composition of the present invention may further comprise a solvent and/or a particulate filler.

Suitable solvents may be selected from water, alcohols such as methanol, ethanol, propanol (n-, i-), butanol (n-, iso-, tert.-), ketones such as acetone or the like.

The photocurable dental composition of the present invention may preferably comprise 5 to 75 percent by weight based on the total weight of the composition of a solvent.

Suitable particulate fillers may be selected from fillers currently used in dental compositions. The filler should be finely divided and preferably has a maximum particle diameter less than about 100 μm and an average particle diameter less than about 10 μm. The filler may have a unimodal or polymodal (e.g., bimodal) particle size distribution.

The filler can be an inorganic material. It can also be a crosslinked organic material that is insoluble in the one or more radical-polymerizable compounds (a), and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

c) optionally milling, classifying and/or sieving the granulation of the coated particulate filler; and d) optionally further crosslinking the granulation of the coated particulate filler; for providing composite filler particles having a median particle size (D50) of from 1 to 70 µm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The photocurable dental composition of the present invention may preferably comprise 0.1 to 85 percent by weight based on the total weight of the composition of particulate filler.

The photocurable dental compositions of the present invention may further contain stabilizers, pigments, free radical scavengers, polymerization inhibitors, reactive and nonreactive diluents, coupling agents to enhance reactivity of fillers, rheology modifiers, and surfactants.

Suitable stabilizers may be selected from reducing agents such as vitamin C, inorganic sulfides and polysulfides and the like.

One-Part or Multi-Part Composition

The photocurable dental composition according to the present invention may be a one-part or a multi-part photocurable dental composition.

The term "one-part" as used herein means that all components of the photocurable dental composition are comprised in one single part.

The term "multi-part" as used herein means that the components of the photocurable dental composition are comprised in a multitude of separate parts. For example, a first part of components is comprised in a first part, while as second part of components is comprised in a second part, a third part of components may be comprised in a third part, a fourth part of components may be comprised in a fourth part, and so on.

Preferably, the photocurable dental composition is a one-part or a two-part photocurable dental composition, most preferably a one-part photocurable dental composition.

For the two-part photocurable dental composition, it is preferred that the coinitiator compound (ii) is contained in a solid part thereof.

For a one or more part photocurable dental composition, it is preferred that the coinitiator compound (ii) is contained in a fluid part thereof having a pH of from 6 to 8.

Use of the Present Polymerization Initiator System (ii)

The polymerization initiator system (ii) described above may be used in a photocurable dental composition, preferably a photocurable dental composition as described above.

For this use, it is preferred that $M^{x+}$ of the sulfinate compound of formula (I) is preferably selected from (1) a iodonium ion of formula (II), (2) a sulfonium ion of formula (III) and a phosphonium ion of formula (IV) as described above.

The present polymerization initiator system (ii) is preferably used in a photocurable dental material selected from the group consisting of a dental composite, a dental glass ionomer cement, a dental cement, and a dental impression material.

The present invention will now be further illustrated based on the following examples and comparative examples. Compounds illustrating the present invention are shown below in Schemes 1 and 2.

1) Initiators and Additives

Scheme 1. Photoinitiators (PPD and CQ) and co-initiator (EDB) or additive (Iod).

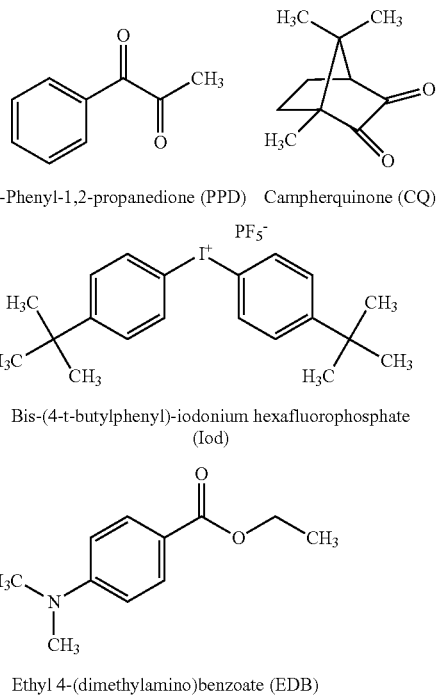

1-Phenyl-1,2-propanedione (PPD)   Campherquinone (CQ)

Bis-(4-t-butylphenyl)-iodonium hexafluorophosphate (Iod)

Ethyl 4-(dimethylamino)benzoate (EDB)

2) Sulfinates

Scheme 2. Sulfinates according to the present invention used as co-initiators.

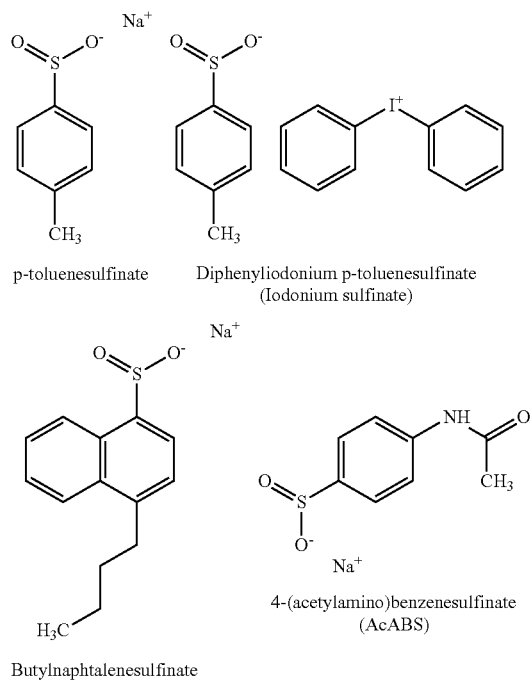

p-toluenesulfinate    Diphenyliodonium p-toluenesulfinate (Iodonium sulfinate)

Butylnaphtalenesulfinate 4-(acetylamino)benzenesulfinate (AcABS)

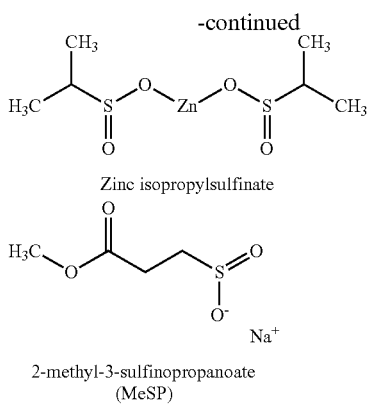

Zinc isopropylsulfinate 2-methyl-3-sulfinopropanoate (MeSP)

2) Sulfonates

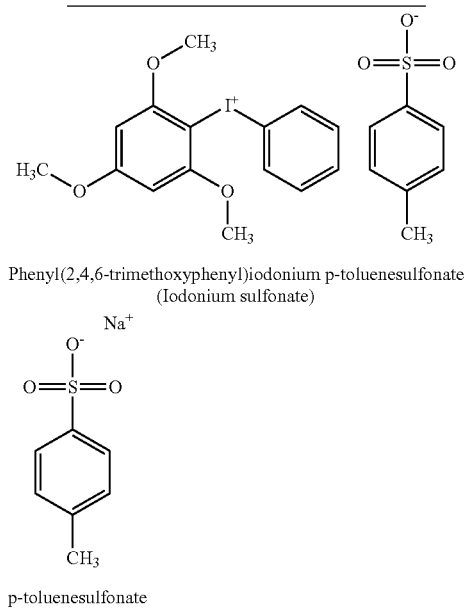

Scheme 3. Sulfonates according to the present invention used as co-initiators.

Phenyl(2,4,6-trimethoxyphenyl)iodonium p-toluenesulfonate (Iodonium sulfonate)

p-toluenesulfonate

Example 1

Aliphatic Sulfinate as Co-Initiator

Figure 1:
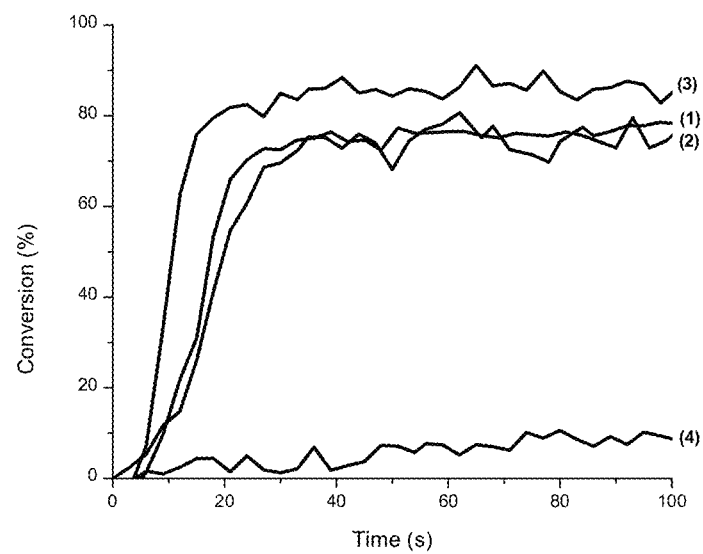
FIG. 1 shows photopolymerization profiles of methacrylate resin (bisGMA/TEGDMA/Methacrylic acid: 63/27/ 10% w/w) in presence of camphorquinone as photoinitiator (under air; thickness=1.4 mm; Smartlite Focus 300 mW.cm$^{-2}$): (1) CQ/zinc isopropylsulfinate (0.5/1% w/w) (2) CQ/zinc isopropylsulfinate/Iod (0.5/1/1% w/w) (3) CQ/EDB (0.5/1% w/w) (4) CQ (0.5%). The irradiation starts at t=5 s.

Sulfinates are shown to be efficient co-initiators for free radical polymerization upon irradiation with blue light for dental materials when used in combination with camphorquinone. The polymerization of bisGMA-TEGDMA resin in the presence of camphorquinone and zinc isopropyl sulfinate (Scheme 1 and 2) is reported in FIG. 1. Excellent final conversions are reached under air and for samples of thickness 1.4 mm for a Dental LED ($\lambda_{max}$=480 nm). Without sulfinate (i.e. for camphorquinone alone), no polymerization occurs showing the co-initiator role of the sulfinate (Curve 4). Moreover, the bleaching properties are found excellent in the presence of sulfinate.

Figure 2:
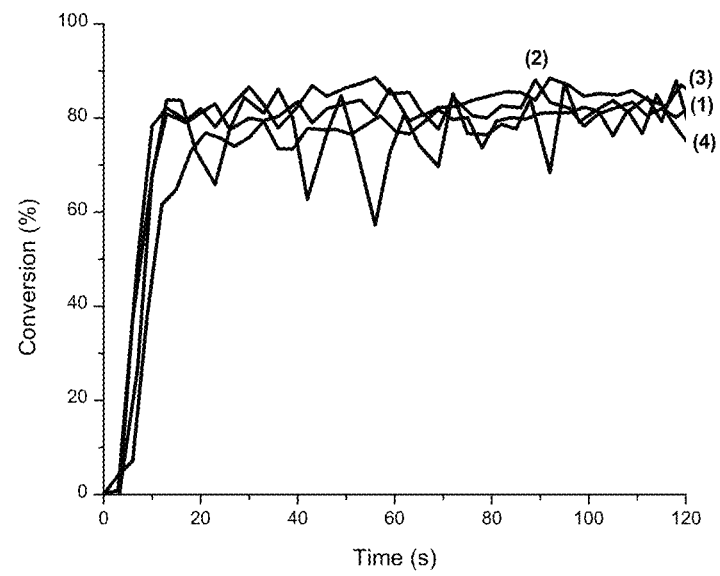
FIG. 2 shows photopolymerization profiles of methacrylate resin (bisGMA/TEGDMA: 70/30% w/w or bisGMA/TEGDMA/2-hydroxyethyl methacrylate: 63/27/10% w/w or bisGMA/TEGDMA/Methacrylic acid: 63/27/10% w/w) in presence of camphorquinone as photoinitiator (under air; thickness=1.4 mm; Smartlite Focus 300 mW.cm$^{-2}$): (1) CQ/MeSP/Iod (0.5/1/1% w/w) in bisGMA/TEGDMA (70/30% w/w) (2) CQ/MeSP/Iod (0.5/1/1% w/w) in 2-hydroxyethyl methacrylate/bisGMA/TEGDMA (10/63/27% w/w) (3) CQ/MeSP/Iod (0.5/1/1% w/w) in Methacrylic acid/bisGMA/TEGDMA (10/63/27% w/w) (4) CQ/EDB (0.5/1% w/w) in bisGMA/TEGDMA (70/30% w/w). The irradiation starts at t=5 s.

1-methyl 3-sulfinopropanoate (MeSP) is shown to be another example of aliphatic sulfinate that can work as an efficient co-initiator for free radical polymerization. The polymerization of bisGMA-TEGDMA resin (also with addition of 2-hydroxyethyl methacrylate or methacrylic acid) in the presence of camphorquinone and the aliphatic sulfinate 1-methyl 3-sulfinopropanoate (Scheme 1 and 2) combined with an iodonium salt (Scheme 1) is reported in FIG. 2. Excellent final conversions are reached under air and for samples of thickness 1.4 mm for a Dental LED ($\lambda_{max}$=480 nm). Remarkably, the performances of CQ/1-methyl 3-sulfinopropanoate/Iod to initiate FRP of methacrylates (bisGMA-TEGDMA) upon irradiation with the Smartlite Focus (300 mW.cm$^{-2}$) overcome the system CQ/EDB in the same conditions (FIG. 2). Amine free systems can be proposed based on the CQ/aliphatic sulfinate/Iod combination.

Example 2

Aromatic Sulfinate as Co-Initiator

Figure 3:
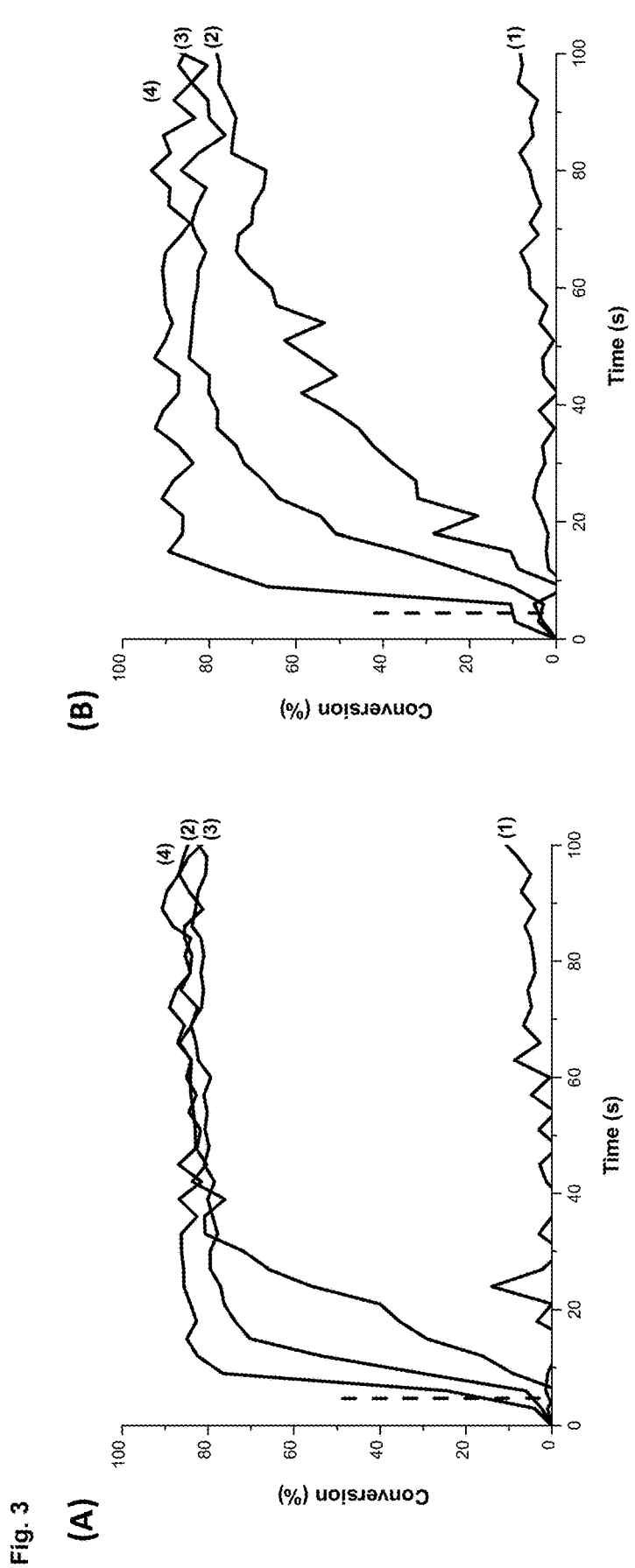
FIG. 3 shows photopolymerization profiles of methacrylate functions (Methacrylic Acid/BisGMA/TEGDMA: 10/63/27% w/w) in presence of (1) PI (1% w) (2) PI/Sulfinate (1/1% w/w) (3) PI/EDB (1/1% w/w) (4) PI/Sulfinate/Iod (1/1/1% w/w) under exposure to Smartlite Focus (300 mW.cm$^{-2}$); sample thickness=1.4 mm; under air; (A) PI=CQ (B) PI=PPD. PI=photoinitiator.

Typical Type II photoinitiators (PIs) exhibit poor reactivity upon light irradiation to initiate free radical polymerization (FRP). Hence, it is necessary to combine them with a co-initiator generally with an amine. But due to the coloration problems observed after storage, finding an alternative to the use of amine as co-initiator is an interesting point. The p-toluenesulfinate (Scheme 2) is proposed in this example as an efficient co-initiator with interesting bleaching properties. For the PI alone (CQ or PPD), no polymerization occurs. Remarkably, in presence of the sulfinate, a good polymerization profile is obtained with a high final conversion (FIG. 3). This performance can be still improved when combined with an iodonium salt.

Remarkably, the performances of CQ/Sulfinate/Iod or PPD/Sulfinate/Iod to initiate FRP of methacrylates (Methacrylic acid/BisGMA/TEGDMA: 10/63/27% w/w) upon irradiation with Smartlite focus (300 mW.cm$^{-2}$) overcome the systems CQ/EDB or PPD/EDB in the same conditions (FIG. 3).

Figure 4:
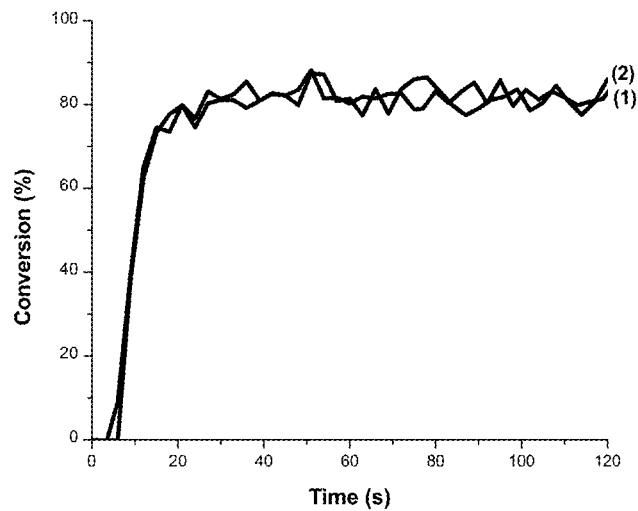
FIG. 4 shows photopolymerization profiles of methacrylate functions (bisGMA/TEGDMA: 70/30% w/w) in presence of camphorquinone as photoinitiator (under air; thickness=1.4 mm; Smartlite Focus 300 mW.cm$^{-2}$): (1) CQ/EDB (0.5/1% w/w) (2) CQ/butylnaphtalenesulfinate/Iod (0.5/1/1% w/w). The irradiation starts at t=5 s.

Other aromatic sulfinates can also be used as co-initiators for free radical polymerization upon blue light in combination with camphorquinone and also in presence of an iodonium salt. For example, the butylnaphtalene sulfinate (Scheme 2) is shown in this example to be an efficient co-initiator for the polymerization of bisGMA-TEGDMA resin upon exposure to a blue dental LED. The polymerization of bisGMA-TEGDMA resin in the presence of camphorquinone and butylnaphtalene sulfinate is reported in FIG. 4. Excellent final conversions are reached under air and for samples of thickness 1.4 mm for a dental LED ($\lambda$max=480 nm). Remarkably, the CQ/butylnaphtalene sulfinate/Iod system exhibits comparable efficiency to the CQ/EDB reference system to initiate FRP of methacrylates.

Figure 5:
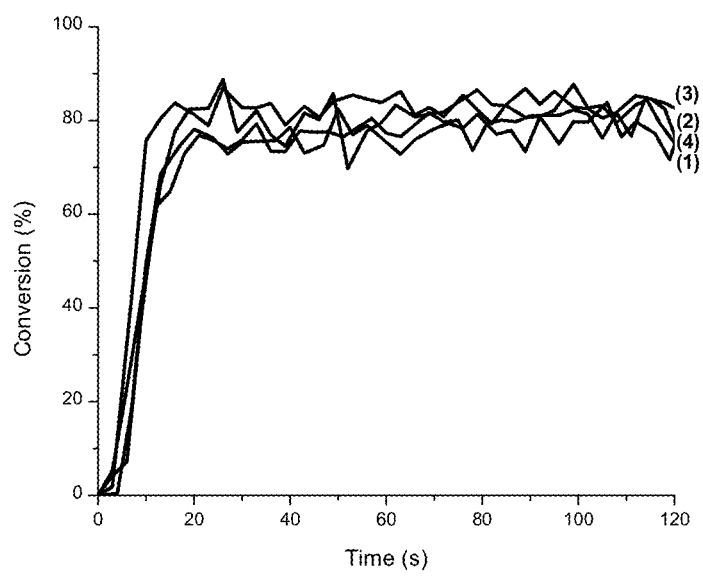
FIG. 5 shows photopolymerization profiles of methacrylate functions (bisGMA/TEGDMA: 70/30% w/w or bisGMA/TEGDMA/2-hydroxyethyl methacrylate: 63/27/10% w/w or bisGMA/TEGDMA/Methacrylic acid: 63/27/10% w/w) in presence of camphorquinone as photoinitiator (under air; thickness=1.4 mm; Smartlite Focus 300 mW.cm$^{-2}$): (1) CQ/AcABS/Iod (0.5/1/1% w/w) in bisGMA/TEGDMA (70/30% w/w) (2) CQ/AcABS/Iod (0.5/1/1% w/w) in 2-hydroxyethyl methacrylate/bisGMA/TEGDMA (10/63/27% w/w) (3) CQ/AcABS/Iod (0.5/1/1% w/w) in Methacrylic acid/bisGMA/TEGDMA (10/63/27% w/w) (4) CQ/EDB (0.5/1% w/w) in bisGMA/TEGDMA (70/30% w/w). The irradiation starts at t=5 s.

4-(acetylamino)benzene sulfinate (AcABS) is also proposed in this example as an aromatic sulfinate and efficient co-initiator for free radical polymerization (Scheme 2). The polymerization of bisGMA-TEGDMA resin (also in presence of 2-hydroxyethyl methacrylate or methacrylic acid) in presence of camphorquinone and 4-(acetylamino)benzene sulfinate (Scheme 2) in combination with an iodonium salt is reported in FIG. 5. Excellent final conversions are reached under air and the CQ/AcABS/Iod system presents similar efficiency than the CQ/EDB reference system for the free radical polymerization of methacrylates (bisGMA-TEGDMA).

Example 3

Good Bleaching Properties for Sulfinates Based Photoinitiating Systems

Figure 6:
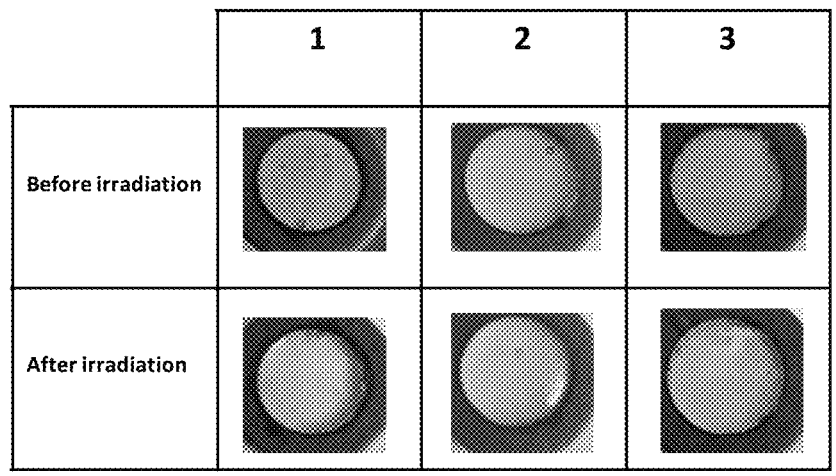
FIG. 6 shows photos of the samples before and after polymerization (under air; thickness=1.4 mm; Smartlite Focus (300 mW.cm$^{-2}$); 115 s irradiation): (1) CQ/zinc isopropylsulfinate/Iod (0.5/1/1% w/w) in Methacrylic acid/bisGMA/TEGDMA (10/63/27% w/w) (2) CQ/MeSP/Iod (0.5/1/1% w/w) in Methacrylic acid/bisGMA/TEGDMA (10/63/27% w/w) (3) CQ/butylnaphtalenesulfinate/Iod (0.5/1/1% w/w) in bisGMA/TEGDMA (70/30% w/w).

Remarkably, good bleaching properties are obtained upon light irradiation for the photoinitiating systems of the present invention based on camphorquinone and sulfinates as co-initiators. In FIG. 6, some examples of photos of the samples before and after polymerization are depicted. Nevertheless, good bleaching properties were obtained for all the investigated sulfinates. The color stability after polymerization is also very good both for storage at room temperature and at 50° C.

Example 4

A New Iodonium-Sulfinate Salt (Ion Exchange Between the Sulfinate and Iodonium Salt)

Figure 7:
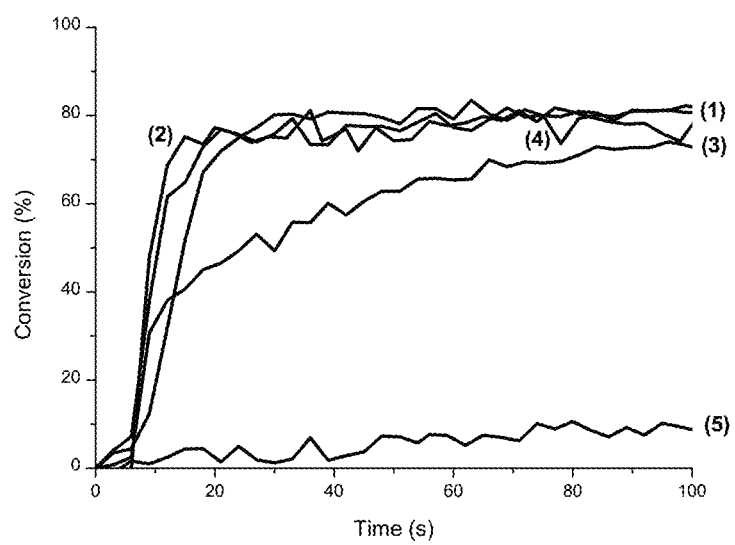
FIG. 7 shows photopolymerization profiles of methacrylate resin (bisGMA/TEGDMA: 70/30% w/w or bisGMA/TEGDMA/2-hydroxyethyl methacrylate: 63/27/10% w/w or bisGMA/TEGDMA/Methacrylic acid: 63/27/10% w/w) in presence of camphorquinone as photoinitiator (under air; thickness=1.4 mm; Smartlite Focus 300 mW.cm$^{-2}$): (1) CQ/iodonium sulfinate (0.5/1% w/w) in 2-hydroxyethyl methacrylate/bisGMA/TEGDMA (10/63/27% w/w) (2)

The sulfinates of the present invention can also be efficient in the presence of iodonium salts in a one-component system through the synthesis of iodonium sulfinate. This new system was synthesized by ion exchange between a sulfinate and an iodonium salt. p-Toluenesulfinate and diphenyliodonium chloride were dissolved in water and mixed together overnight. Chloroform was added to the reaction mixture and the phases were separated. The solvent of the organic layer was evaporated to obtain the new iodonium sulfinate salt (Scheme 4). This one component system can also be efficient in presence of camphorquinone for the polymerization of bisGMA-TEGDMA resin upon exposure to a blue dental LED. The polymerization of bisGMA-TEGDMA resin in presence of camphorquinone and the iodonium sulfinate is reported in FIG. 7. Excellent final conversions are reached under air and for samples of thickness 1.4 mm for a Dental LED (λmax=480 nm). Moreover, excellent bleaching properties are obtained. Remarkably, the CQ/iodonium-sulfinate system is better than the reference CQ/EDB (FIG. 7).

Scheme 4. Structure of the synthesized iodonium sulfinate.

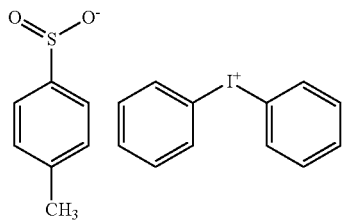

Example 5

Good Bleaching Properties for Iodonium-Sulfinate Based Photoinitiating Systems

Remarkably, the new synthesized iodonium-sulfinate can be used as co-initiator in combination with camphorquinone and leads to good bleaching properties upon light irradiation. The photos of the samples before and after polymerization are depicted in FIG. 8. The color stability after polymerization is also very good.

In the following, experimental tests relating to sulfonate compounds are reported. The investigated sulfonate compounds are shown in Scheme 3 above.

Example 6 p-Toluenesulfonate as Co-Initiator

The sulfonates are efficient co-initiators for free radical polymerization upon irradiation with blue light for dental materials. This new class of co-initiators can be used in the presence of camphorquinone to initiate the free-radical polymerization (FRP) of methacrylates. For example, the polymerization of a bisGMA-TEGDMA blend (also in presence of 2-hydroxyethyl methacrylate or methacrylic acid) in the presence of camphorquinone and p-toluenesulfonate (Scheme 1 and Scheme 3) in combination with an iodonium salt (Iod) is reported in FIG. 9. Excellent final conversions are reached under air and for samples of thickness 1.4 mm upon a representative blue light LED ($\lambda_{max}$=480 nm). Remarkably, the CQ/sulfonate/Iod system exhibits similar performance than the system CQ/amine (ethyldimethylaminobenzoate EDB) reference system to initiate FRP of methacrylates upon irradiation with the Smarlite Focus (300 mW.cm$^{-2}$) in the same conditions (FIG. 9).

Example 7

Iodonium-Sulfonate as Co-Initiator

The sulfonate co-initiators of the present invention can also be efficient in the presence of iodonium salts in a one-component system. The iodonium sulfonate can be used in the presence of camphorquinone for the polymerization of bisGMA-TEGDMA resin upon exposure to a blue dental LED. Phenyl(2,4,6-trimethoxyphenyl)iodonium p-toluenesulfonate (Scheme 3) is shown here as an efficient co-initiator for the polymerization of bisGMA-TEGDMA resin. The polymerization of bisGMA-TEGDMA resin (also in presence of 2-hydroxyethyl methacrylate) in the presence of camphorquinone and iodonium sulfonate is reported in FIG. 10. Excellent final conversions are reached under air and for samples of thickness 1.4 mm for a blue light LED representative of dental materials (λmax=480 nm). Remarkably, the CQ/iodonium sulfonate system exhibits comparable efficiency to the CQ/EDB reference system to initiate FRP of methacrylates (bisGMA-TEGDMA) in the same conditions.

Example 8

Good Bleaching Properties for Sulfonate-Based Photoinitiating Systems

Remarkably, the co-initiators of the present invention in combination with camphorquinone lead to good bleaching properties upon light irradiation. In FIG. 11, the photos of the samples before and after polymerization are depicted. The color stability after polymerization is also excellent.

Application Examples

Composites

The present invention will now be described in further detail with the reference to application examples. The present invention is not limited to the examples described below. The following abbreviations are used hereinafter.
Compounds Used
CQ: Camphorquinone
NapTS: Sodium p-Toluenesulfinate
DMABE: Ethyl 4-(dimethylamino)benzoate
BHT: Butylated hydroxytoluene
Resin and glass filler: Spectrum® TPH®3
Paste Formulation
The given amounts of the respective formulation (table 1, wt % based on resin part) were given to 5 g Spectrum®

TPH®3 resin and 15 g Spectrum® TPH®3 glass filler. Afterwards, the mixture was processed to a paste by using a SpeedMixer.

Procedures

Flexural strength, FS: The flexural strength was measured according to the ISO 4049 guideline (Table 1).

Color stability: The color stability was investigated using following procedure: Three disc specimens of each formula were prepared using a Liculite light oven (irradiation time 90 sec./each side). Afterwards, the initial L*A*B values of each specimen were measured using a Datacolor 800. Specimen 1 was then stored in the dark and dry in the oven at 37±2° C. for 7 days. Specimen 2 was stored in the dark in the oven in water at 37±2° C. for 7 days. Specimen 3 was first stored dark and dry in the oven at 37±2° C. for 24±2 h. After this time, latter specimen was removed from the oven and blanked off half of it with aluminum foil (uncovered side—specimen 3a/covered side—specimen 3b). The specimen was then placed in a radiation chamber immersed in water (37±2° C.) and exposed to the radiation for 24 h at 150 000±15 000 Lux. It was ensured that the water level was 10±3 mm above the specimen. After exposure, the aluminum foil was removed and the specimen was transferred back to the oven at 37±2° C. and stored in the dark and dry for 5 days. The change in color (ΔE) was measured using a Datacolor 800 (Table 2). The ΔE was calculated using following equitation (1):

$$\Delta E = \text{delta} E = \sqrt{\Delta L^{*2} + \Delta a^{*2} + \Delta b^{*2}} \quad (1)$$

TABLE 1

Flexural strength measurements of formula 1-6 of the examples according to the invention and comparative examples.

Application Examples

| Formula | CQ [wt %] | NapTS [wt %] | BHT [wt %] | Flexural strength [MPa] | E-Modulus [MPa] |
|---|---|---|---|---|---|
| A (KJ24-49-1/Run1) | 0.541 | 0.355 | 0.05 | 136 | 9042 |
| B (KJ24-49-1/Run4) | 0.375 | 0.127 | 0.05 | 132 | 8860 |
| C (KJ24-49-1/Run7) | 0.259 | 0.450 | 0.05 | 123 | 8730 |
| D (KJ24-49-1/Run10) | 0.7 | 0.127 | 0.05 | 143 | 9750 |
| E (KJ24-49-1/Run12) | 0.463 | 0.697 | 0.05 | 136 | 9100 |
| F (KJ24-40-01/Run15) | 0.7 | 1.267 | 0.05 | 123 | 8800 |

Comparative Examples

| Formula | CQ [wt %] | DMABE [wt %] | BHT [wt %] | Flexural strength [MPa] | E-Modulus [MPa] |
|---|---|---|---|---|---|
| A (KJ23-119-1/Run1) | 0.541 | 0.355 | 0.05 | 142 | 9240 |
| B (KJ23-119-1/Run4) | 0.375 | 0.127 | 0.05 | 132 | 8950 |
| C (KJ23-119-1/Run7) | 0.259 | 0.450 | 0.05 | 125 | 9250 |
| D (KJ23-119-1/Run10) | 0.7 | 0.127 | 0.05 | 129 | 9230 |
| E (KJ23-119-1/Run12) | 0.463 | 0.697 | 0.05 | 143 | 9720 |
| F (KJ23-119-1/Run15) | 0.7 | 1.267 | 0.05 | 123 | 9350 |

TABLE 2

Results of ΔE measurements of formula A of the examples according to the invention and comparative example.

| | Example (KJ24-49-1/Run1) | | | Comparative Example (KJ23-119-1/Run1) | | |
|---|---|---|---|---|---|---|
| Formula A | Specimen 1 | Specimen 2 | Specimen 3 a/b | Specimen 1 | Specimen 2 | Specimen 3 a/b |
| ΔE | 2.2 | 2.5 | 5.9/1.6 | 4.0 | 4.2 | 20.7/2.5 |

Application Examples

Resin Modified Glass Ionomer (RMGI) Cements Composites

TABLE 3

Formulation of acidic paste

| | Acidic paste 1 (MAB 1-154-1) | |
|---|---|---|
| | [wt.-%] | [g] |
| Polyacrylic acid solution (44 wt.-%) | 83.63 | 16.726 |
| Distilled water | 1.78 | 0.357 |
| Tartaric acid | 5.21 | 1.041 |
| Fumed silica, silanized | 7.93 | 1.586 |
| Camphorquinone | 0.07 | 0.014 |
| N-Benzoylthiourea | 1.38 | 0.276 |
| SUM | 100.00 | 20.00 |

TABLE 4

Formulation of neutral pastes

| | Neutral paste 1 (AG 21-109-3) | | Neutral paste 2 (AG 21-110-3) | |
|---|---|---|---|---|
| | [wt.-%] | [g] | [wt.-%] | [g] |
| 1,3-Bis(acrylamido)-N,N'-diethyl-propane | 18.64 | 3.728 | 18.64 | 3.728 |
| Poly(ethylene glycol) methacrylate | 8.49 | 1.698 | 8.49 | 1.698 |
| Fumed silica, silanized | 6.17 | 1.234 | 6.17 | 1.234 |
| Reactive filler mixture | 44.23 | 8.846 | 44.23 | 8.846 |
| Ytterbium trifluoride | 21.60 | 4.320 | 21.60 | 4.320 |
| Cumenehydroperoxide | 0.76 | 0.152 | 0.76 | 0.152 |
| Sodium-p-toluenesulfinate | 0.11 | 0.022 | 0.00 | 0.000 |
| Zinc-isopropylsulfinate | 0.00 | 0.000 | 0.11 | 0.022 |
| SUM | 100.00 | 20.00 | 100.00 | 20.00 |

TABLE 5

Results for the working time and 3-point bending tests of RMGIs

| | RMGI 1 (acidic paste 1 + neutral paste 1) | | RMGI 2 (acidic paste 1 + neutral paste 2) | |
|---|---|---|---|---|
| Sample | light-cure | dark-cure | light-cure | dark-cure |
| wt [s] | —* | 120 | —* | 110 |
| FS [MPa] | 15 ± 2 | 18 ± 2 | 15 ± 2 | 15 ± 1 |
| FM [MPa] | 790 ± 44 | 890 ± 55 | 1140 ± 73 | 1050 ± 76 |

* gelation after 10 s light-curing

Application Examples

Self-Adhesive Resin Cements (SARCs)

TABLE 6

Formulation of catalyst paste

| | Catalyst paste 1 (MAB 1-174-3) | |
|---|---|---|
| | [wt.-%] | [g] |
| UDMA | 6.60 | 1.320 |
| EBPADMA-Urethane Resin | 6.60 | 1.320 |
| TEGDMA | 4.80 | 0.960 |
| TMPTMA | 6.00 | 1.200 |
| Acrylic acid | 0.51 | 0.102 |
| PENTA | 8.54 | 1.708 |
| BHT | 0.04 | 0.007 |
| Aerosil R711 | 3.00 | 0.600 |
| Silanated EG9726 Glass I | 44.97 | 8.992 |
| Silanated EG9726 Glass II | 18.28 | 3.656 |
| Cumenehydroperoxide | 0.68 | 0.135 |
| SUM | 100.00 | 20.00 |

TABLE 7

Formulation of base pastes

| | Base paste 1 (MAB 1-174-2) | | Base paste 2 (MAB 1-174-1) | |
|---|---|---|---|---|
| | [wt.-%] | [g] | [wt.-%] | [g] |
| UDMA | 3.88 | 0.776 | 3.88 | 0.776 |
| EBPADMA-Urethane Resin | 3.88 | 0.776 | 3.88 | 0.776 |
| TEGDMA | 2.82 | 0.564 | 2.820 | 0.564 |
| TMPTMA | 3.53 | 0.706 | 3.53 | 0.706 |
| HEMA | 7.50 | 1.500 | 7.50 | 1.500 |
| AHPMA | 2.50 | 0.500 | 2.50 | 0.500 |
| BHT | 0.01 | 0.003 | 0.01 | 0.003 |
| Aerosil R711 | 3.00 | 0.600 | 3.00 | 0.600 |
| Silanated EG9726 Glass I | 51.09 | 10.218 | 51.09 | 10.218 |
| Silanated EG9726 Glass II | 21.15 | 4.231 | 21.15 | 4.231 |
| N-Benzoylthiourea | 0.51 | 0.102 | 0.51 | 0.102 |
| Camphorquinone | 0.05 | 0.009 | 0.05 | 0.009 |
| Sodium-p-toluenesulfinate | 0.08 | 0.016 | 0.00 | 0.000 |
| Zinc-isopropylsulfinate | 0.00 | 0.000 | 0.08 | 0.016 |
| SUM | 100.00 | 20.00 | 100.00 | 20.00 |

TABLE 8

Results for the working time and 3-point bending tests of SARCs

| | SARC 1 (catalyst paste 1 + base paste 1) | | SARC2 (catalyst paste 2 + base paste 1) | |
|---|---|---|---|---|
| Sample | light-cure | dark-cure | light-cure | dark-cure |
| wt [s] | —* | 95 | —* | 165 |
| FS [MPa] | 78 ± 20 | 86 ± 19 | 96 ± 13 | 79 ± 11 |
| FM [MPa] | 5180 ± 990 | 4440 ± 160 | 6160 ± 660 | 3890 ± 530 |

* gelation after 10 s light-curing

Preparation

Described amounts of components according to tables 3, 4, 6 and 7 were put in a light-tight plastic container and closed with a lid with a hole in it. Each container was subsequently placed in the SpeedMixer DAC 600-2 VAC-P (Hauschild) and mixed twice at 2500 rpm for 2 min and once at 1000 rpm/100 mbar for 1 min. The hole in the lid was closed with a light-tight scotch tape and containers stored at room temperature until further use.

Testing: Working Time (wt)

Samples were prepared by hand-mixing acidic- and base paste or base- and catalyst paste (1:1, V/V) at 23° C. and ambient light for 30 s. A bead-like body was formed which was periodically probed with a metal instrument. The end of working time was defined by the transition point from viscous, spreadable material to elastic, gel-like one; the start of working time by the beginning of hand-mixing.

Alternatively, samples were hand-mixed for 30 s and then irradiated with a SmartLite Focus for 10 s. Subsequent probing was carried out as described.

Testing: 3-Point Bending

Mechanical data of flexural strength (FS) and flexural modulus (FM) was measured in 3-point bending mode according to ISO 4049:2009. Prior to measurement, hand-mixed samples (n=6) were cured for 2 min. from 2 sides with the light-oven LicuLite (Dentsply DeTrey) and stored in water for 24 h at 37° C. or dark-cured for 1 hour and stored in water for 24 h at 37° C.

The invention claimed is:

1. Photocurable dental composition comprising
   (a) one or more radical-polymerizable compounds,
   (b) a polymerization initiator system containing
      (i) an photoinitiator compound having a light absorption maximum in the range from 300 to 800 nm; and
      (ii) a coinitiator compound;
   wherein the coinitiator compound is a sulfinate compound or a sulfonate compound of the following formula (I):

$$(R-SO_x^-)_y.M^{y+} \quad (I)$$

wherein

R represents an organic moiety;
$M^{y+}$ is a cation, an iodonium ion of the following formula (II):

$$R^1-I^+-R^2 \quad (II)$$

wherein $R^1$ and $R^2$ which are independent from each other represent an organic moiety, or combination thereof,
x is 2 or 3, and
y is an integer of from 1 to 4, and
   (c) a dental particulate filler, wherein the dental particulate filler is selected from the group consisting of quartz, silicon nitride, feldspar, borosilicate glass, kaolin, talc, titania, zinc glass, pulverized polycarbonate, pulverized polyepoxide, and a glass derived from Ce, Sb, Sn, Zr, Sr, Ba, or Al.

2. The photocurable dental composition according to claim 1, wherein R is an aromatic moiety.

3. The photocurable dental composition according to claim 1, wherein R is a phenyl or naphthyl group which may be substituted by 1 to 5 substituents, which may be a same or different and which are independently selected from a group consisting of $C_{1-6}$ alkyl group, a hydroxyl group, an amino group, a halogen atom, and a carboxyl group.

4. The photocurable dental composition according to claim 1, wherein R is an aliphatic moiety.

5. The photocurable dental composition according to claim 4, wherein R is a $C_{1-6}$ alkyl group which may be substituted by a phenyl or naphthyl group which may be substituted by 1 to 5 substituents, which may be a same or different and which are independently selected from a $C_{1-6}$ alkyl group, a hydroxyl group, an amino group, a halogen atom, and a carboxyl group.

6. The photocurable dental composition according to claim 1, wherein the dental composition comprises 0.05 to 5 mole percent of the coinitiator compound based on the one or more radical-polymerizable compounds.

7. The photocurable dental composition according to claim 1, wherein the photoinitiator compound is a 1,2-diketone.

8. The photocurable dental composition according to claim 1, wherein the dental composition comprises 0.05 to 5 mole percent of the photoinitiator compound based on the one or more radical-polymerizable compounds.

9. The photocurable dental composition according to claim 1, wherein the coinitiator compound is contained in a solid part of a two or more part dental composition.

10. The photocurable dental composition according to claim 1, wherein the photocurable dental composition is selected from the group consisting of a dental composite, a dental glass monomer cement, a dental cement, and a dental impression material.

11. The photocurable dental composition according to claim 1, which wherein the polymerization initiator system further comprises an additional electron donor (iii) as a further coinitiator.

12. A method of forming a photocurable dental composition; said method comprising: mixing a polymerization initiator system containing
  (i) a photoinitiator compound having a light absorption maximum in the range from 300 to 800 nm; and
  (ii) a coinitiator compound;
  wherein the coinitiator compound is a sulfinate compound or a sulfonate compound of the following formula (I):

$$(R-SO_x^-)_y M^{p+} \quad (I)$$

wherein
R represents an organic moiety;
$M^{p+}$ is a cation, an iodonium ion of the following formula (II):

$$R^1-I^+-R^2 \quad (II)$$

wherein
$R^1$ and $R^2$ which are independent from each other represent an organic moiety, or combination thereof,
x is 2 or 3and,
y is an integer of from 1 to 4, and
with one or more radical-polymerizable compounds and a dental particulate filler to form the photocurable dental composition, wherein the dental particulate filler is selected from the group consisting of quartz, silicon nitride, feldspar, borosilicate glass, kaolin, talc, titania, zinc glass, pulverized polycarbonate, pulverized polyepoxide, and a glass derived from Ce, Sb, Sn, Zr, Sr, Ba, or Al.

13. The method according to claim 12, wherein the photocurable dental composition is selected from the group consisting of a dental composite, a dental glass ionomer cement, a dental cement, and a dental impression material.

14. The photocurable dental composition according to claim 7, wherein the 1,2-diketone is camphorquinone or tert-butyl (tert-butyldimethylsilyl)-glyoxylate) (DKSi).

15. The photocurable dental composition according to claim 1, wherein the coinitiator compound is contained in a fluid part having a pH of from 6 to 8 of a one or more part dental composition.

16. Photocurable dental composition comprising (a) one or more radical-polymerizable compounds, (b) a polymerization initiator system containing (i) a photoinitiator compound having a light absorption maximum in the range from 300 to 800 nm; and
  (ii) a sulfonate compound of formula:

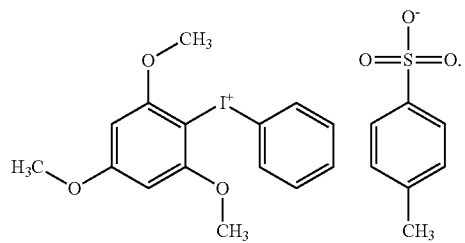 [SMILES: COc1cc(OC)c([I+]c2ccccc2)c(OC)c1 ; Cc1ccc(S(=O)(=O)[O-])cc1]

17. The photocurable dental composition according to claim 1, wherein the dental particulate filler has a maximum particle diameter less than about 100 μm and an average particle diameter less than about 10 μm.

18. The method according to claim 12, wherein the dental particulate filler has a maximum particle diameter less than about 100 μm and an average particle diameter less than about 10 μm.

19. The photocurable dental composition according to claim 1, wherein x is 3 and R is an aromatic moiety.

20. The photocurable dental composition according to claim 1, wherein the dental particulate filler is borosilicate glass.

21. The photocurable dental composition according to claim 1, wherein the dental particulate filler is a glass derived from Ba.

22. The photocurable dental composition according to claim 1, wherein the dental particulate filler is a glass derived from Sb.

23. The photocurable dental composition according to claim 16 further comprising a dental particulate filler, wherein the dental particulate filler is selected from the group consisting of quartz, silicon nitride, feldspar, borosilicate glass, kaolin, talc, titania, zinc glass, pulverized polycarbonate, pulverized polyepoxide, and a glass derived from Ce, Sb, Sn, Zr, Sr, Ba, or Al.

* * * * *